United States Patent [19]
Bridgham et al.

[11] Patent Number: 5,750,346
[45] Date of Patent: May 12, 1998

[54] HOST ORGANISM CAPTURE

[75] Inventors: John A. Bridgham, Hillsborough; John Brandis, Hercules; John Leong, San Francisco; Paul D. Hoeprich, Jr., Danville; Charles L. Sloan, Fremont; Roger A. O'Neill, San Carlos; Charles Andre, Foster City, all of Calif.

[73] Assignee: The Perkin-Elmer Corporation, Foster City, Calif.

[21] Appl. No.: 695,834

[22] Filed: Aug. 7, 1996

Related U.S. Application Data

[63] Continuation-in-part of Ser. No. 585,552, Jan. 11, 1996, which is a continuation-in-part of Ser. No. 511,846, Aug. 7, 1995.

[51] Int. Cl.$^6$ .......................... C12Q 1/68; G01N 33/483; G01N 33/53; C07N 21/04
[52] U.S. Cl. .............................. 435/6; 435/91.2; 435/7.1; 435/7.92; 436/63; 536/23.1
[58] Field of Search ............................... 435/6, 91.2, 210, 435/199, 240, 243, 283.1, 7.1, 7.92; 436/63; 536/23.1

[56] References Cited

U.S. PATENT DOCUMENTS 5,416,000   5/1995   Allen et al. .............................. 435/7.92
5,512,131   4/1996   Kumar et al. .......................... 156/655.1

FOREIGN PATENT DOCUMENTS

WO 96/27132   6/1996   WIPO .................... G10N 33/567

OTHER PUBLICATIONS

Cheung and Fischetti. The role of fibrinogen in staphylococcal adherance to catheters in-vitro. J. Inf. Disease. vol. 161:1177-1186, Jun. 1990.

Wolz et al., Influence of agr on fibrinogen binding in Staphylococcus aureus Newman. Infection and Immun. vol. 64(8):3142-3147, Sep. 1996.

*Primary Examiner*—David Guzo
*Assistant Examiner*—William Sandals
*Attorney, Agent, or Firm*—Paul D. Grossman; Scott R. Bortner

[57] ABSTRACT

Cloning systems useful for the isolation of recombinant nucleic acid are disclosed in which the recombination of cloning-system nucleic acid and foreign nucleic acid is linked to the expression of a moiety on the surface of a host organism, the moiety being a first member of a binding pair. When recombination occurs between the nucleic acid and the foreign nucleic acid, the moiety is expressed on the surface of the host organism. The isolation of recombinant nucleic acid is then performed by attaching a second member of the binding pair to a solid support and contacting the host organism with the support. When the first member of the binding pair is expressed on the surface of the host organism, the host organism binds to the second member of the binding pair attached to the solid support, thereby selectively isolating those organisms. Other aspects of the invention include devices for the isolation of individual cells that differentially express binding moieties on their surface. The devices may be adapted for polynucleotide sequencing and analysis of polynucleotides in the isolated cells. Additional aspects of the invention include methods of using the devices for single cell isolation and analysis.

38 Claims, 13 Drawing Sheets

Covalent Attachment of RNAse to Substrate

HOST ORGANISM CAPTURE

RELATED APPLICATIONS

This application is a continuation in part of U.S. patent application 08/585,552, filed Jan. 11, 1996, which is a continuation in part of U.S. patent application 08/511,846, filed Aug. 7, 1995.

FIELD OF THE INVENTION

The invention is in the field of molecular biology, more particularly, the invention relates to clonal selection of recombinant organisms.

BACKGROUND

This invention relates to the identification and selection of genetically transformed cells. More specifically, this invention describes a vector-host cloning system in which genetic transformation with foreign nucleic acid is accompanied by a measurable change in surface binding properties of a host organism.

The ability to selectively recombine genetic material from different organisms in vitro and to cause the resulting "recombinant" material to be replicated and/or used to direct the expression of proteins in a host organism, has transformed the study of biology and greatly enhanced its practical utility, e.g., Cohen et al., U.S. Pat. No. 4,237,224. Applications of this "cloning" or "recombinant nucleic acid" technology include the expression of medically useful human proteins in bacterial cell culture, the creation of immortalized genetic "libraries" containing the entire genome of a particular organism, and the segregation and replication of foreign nucleic acid in preparation for nucleic acid sequencing.

Generally, the cloning process includes the following steps: (i) foreign nucleic acid fragments are prepared having the appropriate size and cohesive end regions, the foreign nucleic acid being either a digest of genomic nucleic acid or cDNA; (ii) a vector nucleic acid is cleaved with one or more restriction enzymes, preferably at a unique site, to form a vector nucleic acid having cohesive end regions suitable for binding to the cohesive end regions of the foreign nucleic acid fragments, where the vector nucleic acid includes (a) elements which allow the inserted foreign nucleic acid fragments to survive and autonomously replicate in a host organism and (b) a selectable marker in order to facilitate the recognition and isolation of cells carrying the foreign nucleic acid; (iii) the foreign nucleic acid fragments are contacted with the cleaved vector nucleic acid under conditions favoring combination of the foreign nucleic acid fragments and the vector nucleic acid, and the vector and foreign nucleic acid are ligated together, thereby forming a recombinant vector-foreign nucleic acid; (iv) the recombinant vector-foreign nucleic acid is introduced into the host organism, thereby genetically transforming the host organism; (v) the host organisms containing the recombinant vector-foreign nucleic acid are separated from untransformed cells and cells containing only parent vector nucleic acid, and optionally, (vi) the separated cells are subjected to a secondary screen for specific nucleic acid inserts, e.g., by contacting with nucleic acid probes or by contacting their expressed proteins with antibody probes.

A key step in the above cloning process is the identification and isolation of host organisms which have been successfully transformed with recombinant vector-foreign nucleic acid, i.e., step (v) above. A number of products can result from the reaction of the cleaved vector nucleic acid with the foreign nucleic acid fragments. The products of the recombination reaction are a heterogeneous mixture of recombinant vector-foreign nucleic acid molecules together with religated parental vector molecules. In fact, for many systems, the vast majority of cells are transformed with parental vector nucleic acid only, e.g., less than 0.1% of the host organisms are transformed with vector-foreign nucleic acid. This low frequency of vector-foreign nucleic acid transformation creates a large background of cells containing no foreign nucleic acid, thereby dramatically increasing the effort required to perform any secondary screening. The automation of step (v) is a particularly important issue for large-scale cloning projects where millions of potential clones must be screened, e.g., the construction of libraries for genomic sequencing projects.

There are four methods that are commonly used to identify host organisms that contain recombinant vector-foreign nucleic acid, including (i) restriction analysis of small-scale preparations of plasmid nucleic acid, (ii) α-complementation, (iii) insertional inactivation, and, (iv) screening by hybridization (see *Molecular Cloning 2nd Ed.*, Sambrook et al, Chapter 1, Cold Spring Harbor Laboratory Press (1989)).

In the restriction analysis method, a number of independently transformed host organisms are picked from a parent culture and grown up in small-scale cultures. Plasmid nucleic acids are isolated from each culture and then analyzed by digestion with restriction enzymes followed by gel electrophoresis.

In the α-complementation method, the cloning vectors carry a short segment of *Escherichia coli* nucleic acid that contains the regulatory sequences and the coding information for the first 146 amino acids of the β-galactosidase gene (lacZ). Embedded in this coding region is a polycloning site. These vectors are used in combination with host organisms that code for the carboxy-terminal portion of β-galactosidase. While neither the host-encoded nor the vector-encoded fragments are themselves active, they can associate to form an enzymatically active protein. This type of complementation is called α-complementation. The Lac+ bacteria that result from α-complementation are easily recognized because they form blue colonies in the presence of the chromogenic substrate X-gal. However, insertion of a fragment of foreign nucleic acid into the polycloning site of the vector results in the production of an amino-terminal fragment that is not capable of α-complementation. Host organisms carrying recombinant vectors therefore form white colonies. The recombinant vectors can then be visually identified and manually "picked" from the culture.

The insertional inactivation method is used with vectors that carry two or more antibiotic resistance genes and an appropriate distribution of restriction enzyme cleavage sites. The foreign nucleic acid and the vector nucleic acid are digested with restriction enzymes that recognize sites located in only a first antibiotic resistance gene. After ligating the two nucleic acids, the ligation mixture is used to transform *E. coli*. Transformants are selected that are resistant to the second antibiotic. Some of the colonies that grow in the presence of the second antibiotic will contain recombinant vectors; others will contain parental vector nucleic acid that has religated during ligation without insertion of foreign nucleic acid. To discriminate between the two types of transformants, separate plates containing the first or second antibiotic are inoculated with a number of colonies in patches in identical locations. The colonies that grow in the presence of the first antibiotic contain plasmids with active resistance genes, and it is unlikely that such plasmids contain insertions of foreign nucleic acid. It is likely that the colonies that do not grow in the presence of the first antibiotic but do grow in the presence of the second antibiotic carry the foreign nucleic acid sequences.

In hybridization screening techniques, a replica of the host organism colonies is transferred to a filter support, the cells are lysed releasing their nucleic acid, and the nucleic acid is then probed with labeled sequence-specific nucleic acid probes. The location of probe-positive colonies is then used to identify the location of recombinant cells on the original culture plate.

The above methods for identifying cells which have been transformed with recombinant vectors each require a number of cumbersome steps resulting in significant barriers to intelligent automation. Even the most streamlined ($\alpha$-complementation method requires the analyst to (i) grow-up the putatively transformed cells in a culture plate, (ii) visually identify cells having a specified color, (iii) pick cells having a specified color, and (iv) transfer the picked cells to a secondary location. While automated systems for picking individual colonies have been demonstrated, they require complicated robotic and image processing apparatus, making them unsuitable for cost effective, routine application, e.g., Uber et al., *Biotechniques* 11: 642–648 (1991); Jones et al., *Nucleic Acids Research* 20: 4599–4606 (1992). Moreover, because the ($\alpha$-complementation approach requires cells to be plated out, it is not amenable to the selection of cells which can not be grown on culture plates, e.g., certain eukaryotic tissue cells. Additional cumbersome steps in the process of identifying and analyzing cell containing recombinant vectors, as well as other clones of interest, (obtained using ($\alpha$-complementation or other systems) include (i) clonal selection, (ii) capturing multiple cells, (iii) isolation of plasmid DNA, (iv) capturing PCR amplification products, (v) capturing sequence reaction products, (vi) archiving host cell, (vii) archiving plasmids, and (viii) archiving PCR amplification products.

SUMMARY

The present invention is directed toward our discovery of a cloning system which facilitates the isolation of recombinant nucleic acid. Our system links the recombination event to the expression of a moiety at the surface of a host organism such that when recombination occurs, the moiety is expressed on the surface of the host, and in the absence of recombination, the moiety is not expressed on the surface of the host. Moreover, this differentially-expressed moiety is a member of a binding pair, the other member of which is attached to a solid support. Thus, when the moiety is expressed on the surface of the host organism, the host organism can be captured by binding to the solid support. The invention includes methods, apparatus, and compositions for using the cloning system.

An aspect of the invention is to provide a cloning system which is well suited for practical, low-cost automation of the recombinant selection process.

A further aspect of the invention is to provide a cloning system which does not, as with traditional methods of analysis do, require growing host organisms on a culture plate to identify and isolate cells which have been transformed with recombinant nucleic acid.

An additional aspect of our invention is to provide a cloning system which does not require visual identification of host organisms which have been transformed with recombinant nucleic acid.

Another aspect of our invention is to provide a cloning system which does not require mechanically picking selected cells from a culture plate.

Yet another aspect of our invention is to provide a cloning system which results in the placement of recombinant-transformed organisms at discrete, pre-defined locations on a solid support, each location containing only a single recombinant organism.

In a first aspect, the fore going and other objects of our invention are achieved by a cloning system referred to herein as the "trans cloning system," such system including a vector nucleic acid for expression in a host cell. The vector nucleic acid of the trans cloning system includes a repressor gene coding for a repressor and a first promoter sequence for promoting the expression of the repressor gene. The repressor gene contains an insertion site located such that when a foreign nucleic acid is inserted at the insertion site, expression of the repressor gene is insertionally inactivated. The vector further includes a surface-expressed moiety gene for directing the expression of a surface expressed moiety. An operator is functionally linked to the expression of the surface-expressed-moiety gene such that when the repressor is bound to the operator, expression of the surface-expressed-moiety gene is repressed.

One embodiment of the first aspect of the present invention includes a method for cloning and isolating recombinant nucleic acids using the above-described trans cloning system. In the method, the vector is cleaved at the insertion site forming a cleaved vector nucleic acid, and the cleaved vector is contacted with a foreign nucleic acid under conditions sufficient to incorporate the foreign nucleic acid into the cleaved vector nucleic acid, thereby forming a recombinant nucleic acid. The recombinant nucleic acid is inserted into a host organism and the host organism is grown up for a time sufficient to express the surface-expressed moiety gene. The host organism is then contacted with a solid support having attached thereto a binding moiety capable of specifically binding to the surface-expressed moiety (SEM). By limiting the size of the region on the solid support having the binding moiety, single cells may be isolated, i.e., clonal selection.

In a second aspect referred to herein as the "cis cloning system", the present invention provides a nucleic acid capable of express ion in a host organism useful for the isolation of recombinant nucleic acid which includes a surface-expressed-moiety gene along with a promoter sequence for promoting the expression of the surface-expressed-moiety gene. The nucleic acid of the invention further includes a first insertion site located downstream from the promoter sequence and upstream from the surface-expressed-moiety gene and a second insertion site located between the first insertion site and the surface-expressed-moiety gene. Finally, the nucleic acid of the invention includes an expression blocking sequence, located between the first insertion site and the second insertion site, which serves to block the expression of nucleic acid sequence located downstream from the expression blocking sequence, e.g., the surface expressed moiety (SEM) gene.

In one preferred embodiment, the present invention provides a method for cloning and isolating recombinant nucleic acid using the above described nucleic acid. In the method, the nucleic acid is cleaved at the first insertion site and at the second insertion site thereby forming a cleaved nucleic acid. Next, the cleaved nucleic acid is mixed with a foreign nucleic acid under conditions sufficient to incorporate the foreign nucleic acid into the cleaved nucleic acid, thereby forming a recombinant nucleic acid. The recombinant nucleic acid is then inserted into a host organism and the host organism is grown up for a time sufficient to express the surface expressed moiety gene. Finally, the host organism is contacted with a solid support having attached thereto a moiety capable of specifically binding to the surface expressed moiety.

In yet another aspect referred to herein as the "tag cloning system", the present invention provides a cloning system useful for the isolation of recombinant nucleic acid which includes a tag moiety sequence which is adapted for linking to a foreign nucleic acid thereby forming an insertion sequence. In addition to the tag moiety sequence, the system includes a nucleic acid having a surface-protein gene coding for a protein which is expressed on the surface of a host organism. The nucleic acid further includes a promoter sequence for promoting the expression of the surface-protein gene and an insertion site located within the surface protein gene such that when the insertion sequence is inserted at the insertion site, the tag moiety sequence is expressed at the surface of the host organism.

One embodiment of the present invention includes a method for cloning and isolating recombinant nucleic acid using the above-described tag cloning system. In this method, the nucleic acid of the invention is cleaved at the insertion site thereby forming a cleaved nucleic acid. The tag moiety sequence is then linked to a foreign nucleic acid forming an insertion sequence. Next, the insertion sequence is contacted with the cleaved nucleic acid under conditions sufficient to incorporate the insertion sequence into the cleaved nucleic acid, thereby forming a recombinant nucleic acid. The recombinant nucleic acid is then inserted into a host organism and the host organism is grown up for a time sufficient to express the tag moiety sequence. Finally, the host organism is contacted with a solid support having attached thereto a moiety capable of specifically binding to the tag moiety.

In yet another aspect, referred to herein as the "lethal gene inactivation system", the present invention provides a nucleic acid capable of expression in a host organism useful for the isolation of recombinant nucleic acid. The nucleic acid of the invention includes a surface-expressed-moiety gene along with a first promoter sequence for promoting the expression of the surface-expressed-moiety gene. The nucleic acid of the invention further includes a lethal gene whose expressed protein is lethal to the host organism and a second promoter sequence for promoting the expression of the lethal gene. Finally, the nucleic acid includes an insertion site located within the lethal gene such that when foreign nucleic acid is inserted at the insertion site the lethal gene is insertionally inactivated.

In one preferred embodiment, the invention includes a method for cloning and isolating recombinant nucleic acid using the lethal gene inactivation system. In this method, the nucleic acid of the invention is cleaved at the insertion site. The cleaved nucleic acid is then contacted with a foreign nucleic acid under conditions sufficient to incorporate the foreign nucleic acid into the cleaved nucleic acid, thereby forming a recombinant nucleic acid. The recombinant nucleic acid is then inserted into a host organism and the host organism is grown up for a time sufficient to express the lethal gene and the SEM gene. Finally, the host organism is contacted with a solid support having attached thereto a moiety capable of specifically binding to the SEM.

In yet another aspect, the present invention provides a host organism capture system. The system includes a solid support having a plurality of binding moieties attached thereto. The binding moieties are members of binding pairs, the complementary member of the binding pairs being differentially expressed on the surface of a host organism using any one of the above-described cloning systems. Alternatively, the binding moieties may be selected so as to be complementary to a binding pair member on the surface of a cell of interest, wherein the surface expressed binding pair member is not differentially expressed. Preferably the binding moieties are located in a plurality of discrete anchor sites 10, each anchor site having dimensions such that only a single host organism can bind to a single anchor site 10.

The host organism capture system may also comprise a plurality of incubation chambers 50, each chamber enclosing a single anchor site 10 in a liquid occlusive manner. The incubation chambers 50 may be used to provide for the growth of captured cells and/or performing biochemical reactions on polynucleotides derived from the captured cells or the progeny of the captured cells. Embodiments of the host organism capture systems of the invention may also comprise a cover plate 40. The cover plate 40 may comprise a plurality of capture regions 60 in register with the incubation chambers 50. The capture regions 60 may be cell capture regions formed of binding pair moieties that are members of binding pairs complementary to binding pair members expressed on the surface of cells of interest. In other embodiments of the host organism capture system, capture regions may be located on the walls of the incubation chambers 50. The host capture system may further comprise DNA capture regions formed of DNA binding reagents. Similarly, the host capture systems may further comprise sequence-specific DNA capture regions formed of polynucleotides (or synthetic analogs thereof) having a specific binding sequence or sequences.

Another aspect of the invention is to provide methods for analyzing individual cells of interest. The methods involve contacting a liquid containing a cell population to a host organism capture system of the invention. The contact results in single cells expressing binding pair members on their surface being bound to anchor sites 10 on the host organism capture system. Single cells that have been bound to the anchor regions may be lysed in situ, thereby releasing polynucleotides for further analysis, e.g., by PCR or nucleic acid sequencing. Alternatively, the single cells that have been bound to the anchor site 10 may be propagated so as to produce progeny cells. Such progeny cells may be bound to cell capture regions, thereby permitting the archiving of the progeny cells. Additionally, the progeny cells may be lysed to release polynucleotides for further analysis, e.g., by PCR or nucleic acid sequencing.

These and other objects, features, and advantages of the present invention will become better understood with reference to the following description, drawings, and appended claims.

DESCRIPTION OF PREFERRED EMBODIMENTS

Generally, the present invention is directed toward our discovery of cloning systems useful for the isolation of recombinant nucleic acid. These systems link the recombination of vector nucleic acid and foreign nucleic acid to the expression of a moiety which is located at the surface of a host organism, the moiety being a first member of a binding pair. When recombination occurs between vector nucleic acid and foreign nucleic acid, the moiety is expressed on the surface of the host organism. Alternatively, when no recombination occurs, the moiety is not expressed on the surface of the host organism. The isolation of the recombinant nucleic acid is then performed by attaching a second member of the binding pair to a solid support and contacting the host organism with the support. When the first member of the binding pair is expressed on the surface of the host organism, the host organism binds to the second member of the binding pair attached to the solid support, thereby selectively removing those organisms from the host-organism suspension. In this way host organisms containing recombinant nucleic acid can be physically isolated from host organisms which lack such nucleic acid. Furthermore, by limiting the size of the region on the solid support having the binding moiety, single cells may be isolated, i.e., clonal selection is achieved.

1. Trans Cloning System

In a first aspect of the present invention, hereinafter referred to as the "trans cloning system", the recombination of vector nucleic acid and foreign nucleic acid is linked to the expression of a surface-expressed moiety through the disruption of a repressor gene. When recombination has occurred, the repressor gene is insertionally inactivated, thereby allowing the expression of a SEM gene which is functionally linked to an operator which binds the repressor. Therefore, in the absence of recombination, a functional repressor is expressed, leading to the repression of the SEM gene. As used herein, "repressed" means that the level of expression is reduced by at least a factor of three relative to the level of expression observed in the absence of repression.

Figure 1:
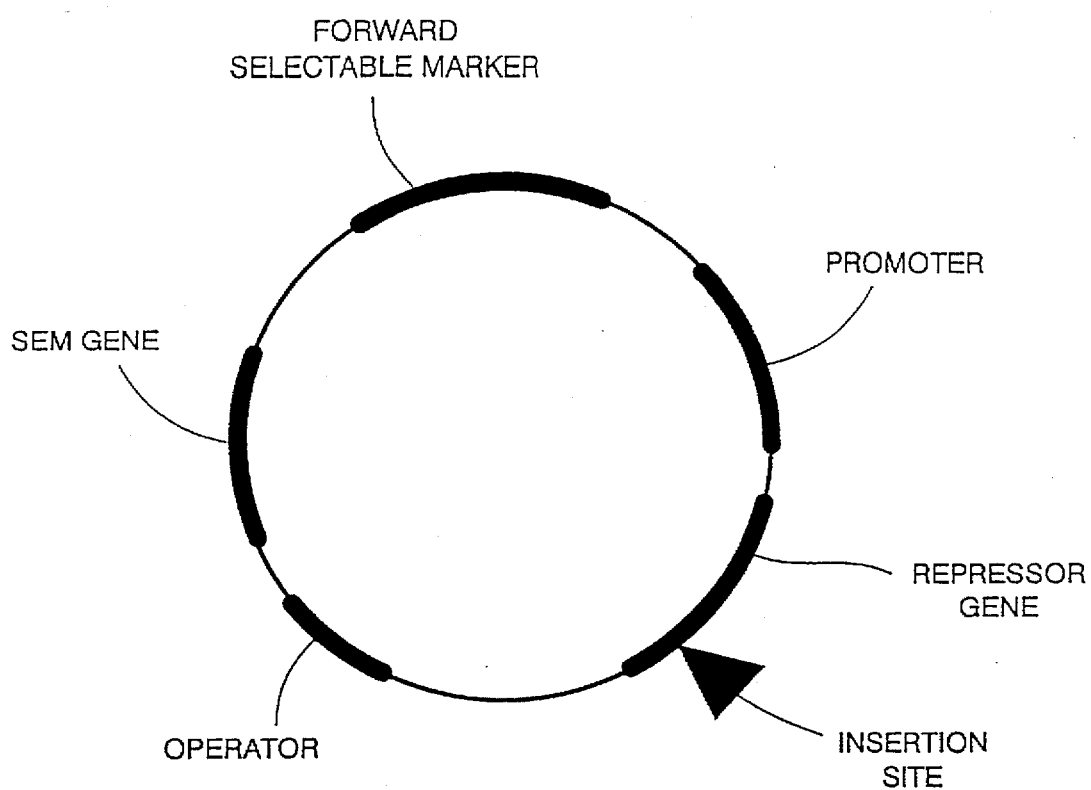
FIG. 1 shows a schematic diagram of the trans cloning system of the present invention.

In the preferred embodiment shown in FIG. 1, the vector nucleic acid includes (i) a repressor gene; (ii) an insertion site located within the repressor gene or its associated promoter such that when a foreign nucleic acid is inserted at the insertion site, the repressor gene is insertionally inactivated; (iii) a promoter functionally linked to the repressor gene for promoting expression of the repressor gene; (iv) a SEM gene for directing the expression of a surface-expressed moiety; and (v) an operator functionally linked to the SEM gene such that when a repressor is bound to the operator, expression of the SEM gene is repressed.

As used herein, the term "insertion site" refers to a location on a double or single stranded nucleic acid at which the nucleic acid may be cleaved in a sequence-specific manner, using a restriction endonuclease or any other like sequence-specific cleaving means, such that properly treated foreign nucleic acid may be ligated therein, e.g., a restriction site. As used herein, the term "ligate" refers to the joining of two strands of nucleic acid by either enzymatic means, e.g., using T4 nucleic acid ligase, *E. coli* nucleic acid ligase, or other like nucleic acid ligases, e.g., Current Protocols in Molecular Biology, Ausubel et al. eds., *Current Protocols* (1993), or using chemical means, e.g., Herrlein et al., *Nucleic Acids Research*, 22: 5076–78 (1994), and Shabarova et al., *Nucleic Acids Research*, 19: 4247–51 (1991).

In the present invention, the purpose of the vector nucleic acid is to (I) provide a means for the transport of foreign nucleic acid into a host organism, (ii) provide for the maintenance and/or replication of the foreign nucleic acid in the host organism, and (iii) provide a linkage between genetic recombination and the expression of the SEM molecule at the surface of the host organism. Preferred vectors may be based on plasmids, cosmids, viruses, or retroviruses, e.g., M13mp, bacteriophage λ, cos 202, cos 203, bovine papilloma virus, Epstein-Barr virus, or any other like vectors, e.g., *Molecular Cloning Second Edition*, Sambrook et al, eds., Cold Spring Harbor Laboratory Press (1989). The vector nucleic acid may be either linear or circular in form. However, preferably the vector nucleic acid is a circular plasmid.

As used herein, the term "repressor" refers to molecules which act to inhibit the expression of a target structural gene by binding to a specific operator functionally linked to the target structural gene, and the term "repressor gene" refers to a gene which codes for the repressor molecule. The term "operator" as used herein refers to a specific site on a nucleic acid at which a repressor specifically binds, such specific binding blocking the expression of an associated structural gene. Typically, repressors act by preventing the transcription of a structural gene into MRNA by blocking the attachment of RNA polymerase to the nucleic acid. Therefore, when repressor molecules are not present, RNA polymerase can bind to nucleic acid and initiate transcription, and, when repressor molecules are present, the RNA polymerase is prevented from binding to the nucleic acid, and transcription, and therefore expression, is effectively blocked.

The repressor gene may be either constitutively expressed or inducibly expressed. Preferably, the repressor gene is constitutively expressed. More preferably, the repressor gene is overexpressed, where, as used herein, the term "overexpressed" refers to a level of expression which is greater than normal physiological levels. Such constitutive overexpression provides tight control of the expression of the structural gene with which the repressor molecule is associated.

Preferred repressor-operator systems include the lac operon, the gal operon, the alpha2-ste6 system, the cI repressor of the $\lambda_{PL}$ promoter, or any other like repressor-operator system, e.g., Maximizing Gene Expression, Reznikoff et al., Butterworths (1986).

In an important feature of the present invention, an insertion site is located within the repressor gene, where, as used herein, the term "insertion site" refers to a location on a nucleic acid at which the nucleic acid can be cleaved at a sequence-specific location using a sequence-specific cleaving agent, e.g., a restriction enzyme, or chemical cleaving agents, e.g., Dervan, Nature 359: 87–88, and foreign nucleic acid can be inserted. The location of the insertion site within the repressor gene is such that when a foreign nucleic acid is inserted at the site, the expression of the repressor gene is effectively inactivated, i.e., the repressor gene is insertionally inactivated. Typically, an insertion site is a nucleic acid sequence at which one or more restriction enzymes specifically cut the nucleic acid, the ends of the cuts being such that properly treated foreign nucleic acid can be ligated into the insertion site. Preferably, the insertion site may be cut by a plurality of different restriction enzymes or other sequence-specific cutting agents, thereby providing greater flexibility as to the types of foreign nucleic acids which can be accommodated. Numerous such restriction enzymes are available from commercial sources, each enzyme recognizing a different nucleic acid sequence, e.g., Stratagene Cloning Systems, La Jolla Calif., 1994 Catalog. Preferably, the restriction site defining the insertion site occurs only once in the vector nucleic acid so that the insertion site is uniquely defined in the vector, e.g., cleaving agents which recognize sequences of at least six bases in length.

In one preferred embodiment of the present invention, the vector nucleic acid includes a promoter for promoting the expression or overexpression of the repressor gene. The promoter may be either constitutive, e.g., tet promoter, bla promoter, or any other like constitutive promoter, or regulatory, e.g., lac, $\lambda_{PL}$, Tac, or any other like regulatory promoter. The promoter is located so as to be functionally linked to the expression of the repressor gene. Preferably, the promoter is regulatory.

Preferably, the vector nucleic acid of the present invention further includes a forward selectable marker for selecting between transformed and untransformed host organisms. Preferred forward selectable markers include genes conferring antibiotic resistance. Thus, when a population of host organisms is challenged with a selection agent, e.g., an antibiotic, only those organisms which have been transformed with the vector nucleic acid will survive. Exemplary forward selectable markers include the $amp^R$ gene.

The vector nucleic acid of the trans cloning system further includes a SEM gene which codes for a moiety that is expressed in the host, then transported to the surface of the host such that it is presented to the exterior surface of the host organism. Moreover, the SEM is a member of a binding pair, where, as used herein, the term "binding pair" refers to a pair of molecular entities, e.g., binding moieties, which specifically and strongly bind to one another under suitable conditions, one member of the binding pair being differentially expressed on the surface of a host organism, and the other member of the binding pair being attached to a solid support. Exemplary binding pairs include ligand/receptor pairs, antigen/antibody pairs, the biotin/avidin pair, and the like. A more thorough discussion of the properties of preferred SEM molecules and preferred binding pairs will be presented in a following section.

The vector also includes an operator associated with the SEM gene which serves to regulate the expression of the SEM gene. Moreover, the operator is functionally linked to the expression of the SEM gene such that when the repressor is bound to the operator, expression of the SEM gene is repressed. Preferably the operator is located upstream from the SEM gene. As used herein the term "upstream" refers to a direction towards the 5' end of a sense strand of a double-stranded nucleic acid, and the term "downstream" refers to a direction towards the 3' end of a sense strand of a double-stranded nucleic acid. Preferred operator/repressor pairs have been discussed above.

The host organism may be eukaryotic, viral, or bacterial. Suitable eukaryotic cells include yeast cells, mammalian cells, and plant cells. The host organism must be (i) capable of being transformed with the vector nucleic acid and (ii) provide a suitable environment for the maintenance and/or replication of the vector nucleic acid and the host nucleic acid. Exemplary host organisms include COS cells, CHO cells, E. coli, or any other suitable host organism. Preferably, the host organism is a bacteria, e.g., E. coli.

Figure 5:
FIG. 5 shows a proposed E. coli K-12 host strain useful in the trans cloning system of the invention.
Figure 6:
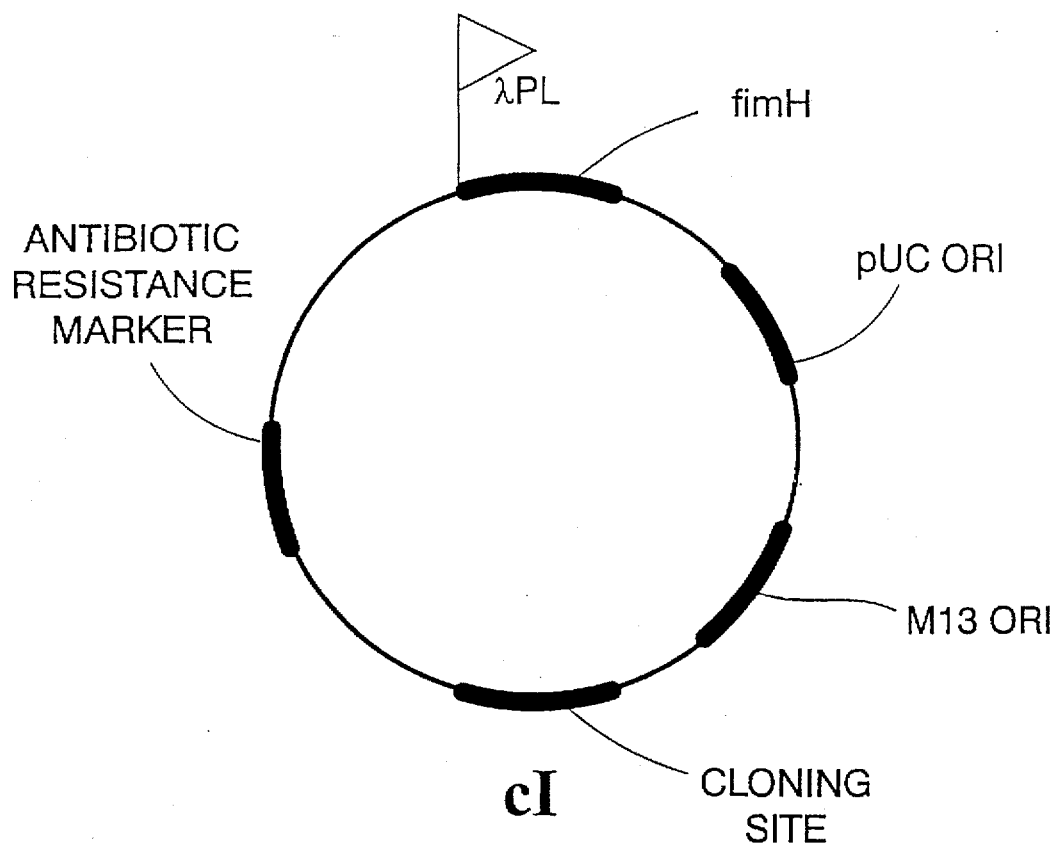
FIG. 6 shows a proposed plasmid for the trans cloning system of the invention.

One particularly preferred host/vector trans cloning system is based on a modified host E. coli K-12 strain. In this strain, the regulatory fimE and fimB genes, and the fimH gene are deleted causing the resulting host strain to be non-fimbriated and "locked on" for type 1 fimbriae when complemented in trans with a wild-type fimH gene (FIG. 5). The preferred minimal elements of a cloning plasmid in this preferred system include an antibiotic resistance marker, a pUC replicon for high-copy number, an M13 origin of replication, the fimH gene cloned behind the lambda left promoter, and the cI repressor gene of lambda (FIG. 6). When the above E. coli host strain is transformed with this plasmid, the resulting transformant will still be non-fimbriated because the cI protein will repress the fimH gene, resulting in lack of complementation. When foreign DNA is cloned into the cI gene, the cI gene will be insertionally inactivated, relieving the repression of the fimH gene and consequently complementing the fimH defect in the chromosome. The resulting host will become frmbriated and hence capable of capture on an RNAse B-functionalized substrate. A plasmid cloning system based upon insertional inactivation of the lambda cI857 repressor gene has been previously described, e.g., P. J. Solenberg and S. G. Burgett, J. Bacteriol. 171: 4807–4813 (1989).

Methods utilizing the trans cloning system utilize cloning techniques well known in the art of molecular biology. First, the vector nucleic acid is cleaved at the insertion site using an appropriate restriction endonuclease under conditions sufficient to render the restriction enzyme active. The cleaved vector nucleic acid is contacted with a foreign nucleic acid under conditions sufficient to incorporate the foreign nucleic acid into the vector nucleic acid at the insertion site, e.g., by enzymatic ligation, thereby forming a recombinant vector nucleic acid. The recombinant vector nucleic acid is then inserted into the host organism by either transfection, transformation, or conjugation, the particular mode of insertion being dependent on the nature of the recombinant vector nucleic acid and the host organism. The host organism is then grown up to provide an opportunity for the expression of the surface-expressed moiety. Finally, the host organism is contacted with a solid support which has been functionalized with a moiety capable of specifically binding to the SEM (see below). If a particular host organism contains a recombinant vector nucleic acid, the host organism will express the SEM at its outer surface and will therefore bind to the functionalized solid support.

2. Cis Cloning System

In a second aspect In a second aspect of the present invention, hereinafter referred to as the "cis cloning system,"

the recombination of vector nucleic acid and foreign nucleic acid is linked to the expression of a SEM by linking the recombination event with the removal of a segment of vector nucleic acid which blocks the expression of the SEM gene.

Figure 2:
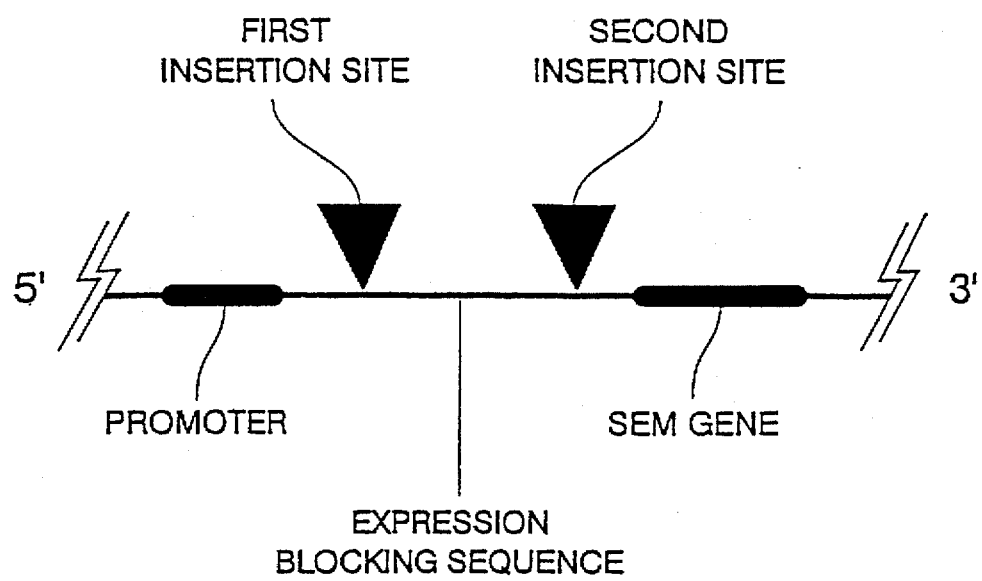
FIG. 2 shows a schematic diagram of the of cis cloning system of the present invention.

As shown in FIG. 2, the preferred vector nucleic acid of the cis cloning system includes five elements: (i) a promoter sequence, (ii) a first insertion site, (iii) a second insertion site, (iv) an expression blocking sequence, and (v) a SEM gene. Preferably, the vector is a circular nucleic acid.

The purpose of the promoter sequence is to promote the expression of downstream nucleic acid sequence, particularly the SEM gene. Preferred promoter sequences have been previously described herein.

Preferably, the first and second insertion sites are chosen such that different restriction enzymes cleave each site, and that each restriction site occurs only once in the vector nucleic acid. By making each of the two restriction sites different from the other, the opportunity for religation of the parent vector after restriction without incorporation of the foreign nucleic acid is reduced, and, cDNA fragments, for example, may be directionally inserted.

In a significant feature of the present invention, the nucleic acid sequence located between the first and second insertion sites forms an expression blocking sequence (EBS), where as used herein, the term "expression blocking sequence" refers to a nucleic acid sequence which serves to block the expression of downstream nucleic acid, particularly the SEM gene. The EBS is located between the first and second insertion sites forming a removable "EBS cassette."

One preferred embodiment of the EBS acts by blocking the translation of mRNA transcribed from the EBS and associated downstream transcript by ribosomes. Such an EBS is referred to herein as a "translation blocking sequence". A preferred translation blocking sequence includes a sequence which, when transcribed into mRNA, forms a hairpin or other like self-associated structure in the mRNA molecule, e.g., tetra loops, stem loops, pseudo knots, and the like. By forming such a self-associated structure, the efficiency of translation of downstream messenger nucleic acid sequence is greatly reduced.

A second preferred embodiment of the EBS acts by reducing the efficiency of transcription of nucleic acid sequence into mRNA, such a sequence being referred to herein as a "transcription blocking sequence." Rather than disrupting the ribosome-mRNA interaction, the transcription blocking sequence interferes with the RNA-DNA-polymerase interaction. Many such transcription blocking sequences are well known, e.g., stem loops. Preferably, the EBS contains multiple transcription blocking sequences arranged serially.

A third preferred embodiment of the EBS utilizes both a translation blocking sequence and a transcription blocking sequence to block the expression of downstream nucleic acid.

The SEM gene in the cis cloning system is located downstream from the EBS and is physically linked to the EBS such that when the EBS is present, expression of the SEM gene is blocked. Otherwise, the SEM gene performs essentially the same function and has the same properties as the SEM gene described above with reference to the trans cloning system.

The host organism in the cis cloning system serves to provide an environment suitable for maintenance and/or replication of the vector nucleic acid.

Methods employing the cis cloning system utilize cloning techniques well known in the art of molecular biology. First, the vector nucleic acid is cleaved at the first and second insertion sites using an appropriate cleaving agent or combination of cleaving agents under reaction conditions sufficient to render all the cleaving agents active. In the event that the reaction conditions of the two agents are not compatible, two separate reactions may be performed serially. This double cleavage reaction serves to remove the EBS cassette.

The cleaved vector nucleic acid is then contacted with a foreign nucleic acid under conditions sufficient to incorporate the foreign nucleic acid into the vector nucleic acid between the first and second insertion sites, e.g., by enzymatic ligation, thereby forming a recombinant vector nucleic acid. The recombinant vector nucleic acid is then inserted into the host organism by either transfection, transformation, or conjugation, the particular mode of insertion being dependent on the nature of the recombinant vector nucleic acid and the host organism. The host organism is then grown up to provide an opportunity for the expression of the surface-expressed moiety. Finally, the host organism is contacted with a solid support which has been functionalized with a moiety capable of specifically binding to the SEM (see below). If a particular host organism contains a recombinant vector nucleic acid, the host organism will express a SEM at its outer surface and will therefore bind to the functionalized solid support.

3. Tag Insertion Cloning System

In yet a third aspect of the present invention, hereinafter referred to as the "tag insertion cloning system", the recombination of vector nucleic acid and foreign nucleic acid is linked to the expression of a tag moiety (TM) on the surface of the host organism by linking the recombination event with the insertion of a tag moiety sequence into a gene for a protein which is normally expressed on the surface of the host organism. By inserting the TM sequence into the surface-protein gene, the product of the tag moiety sequence is presented to the outside surface of the host organism.

Figure 3:
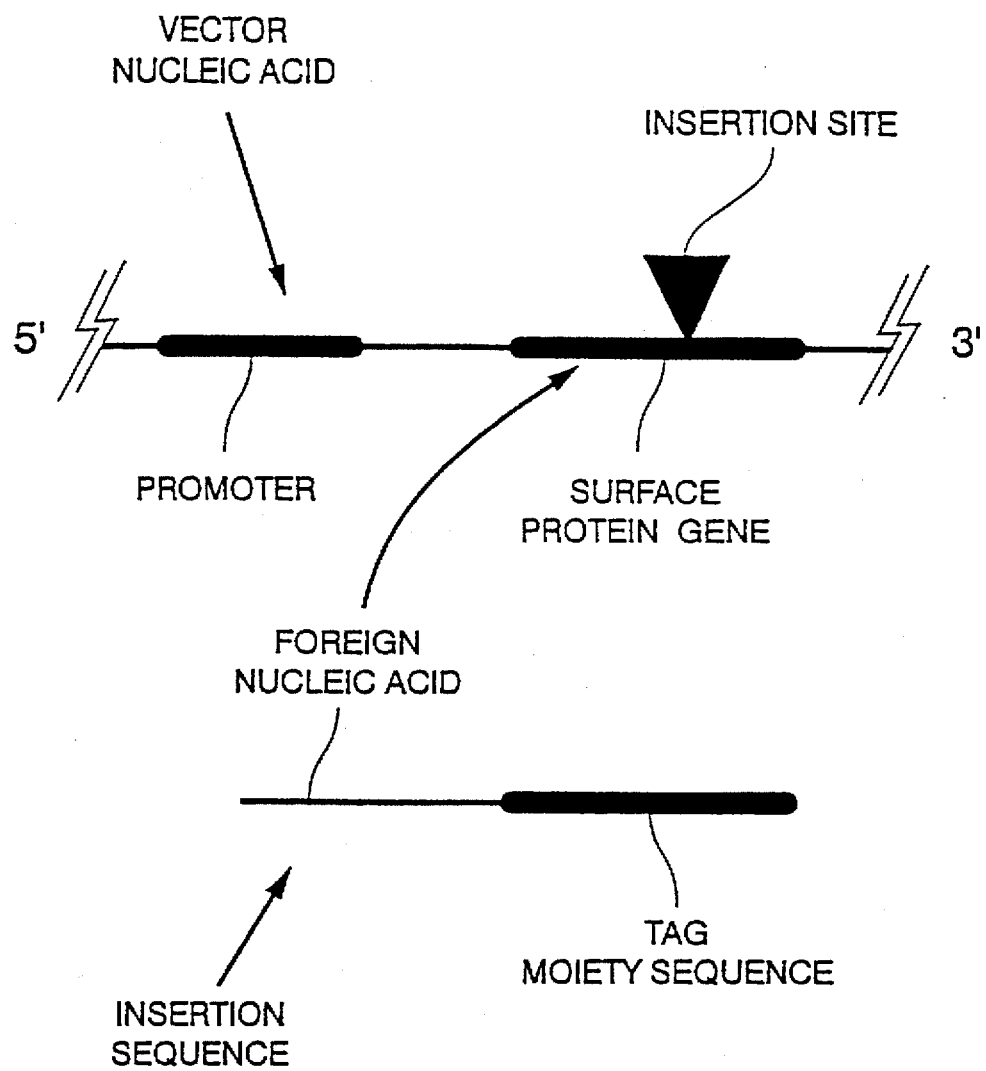
FIG. 3 shows a schematic diagram of the tag cloning system of the present invention.

As shown in FIG. 3, the tag cloning system includes (I) a vector nucleic acid, the vector nucleic acid including (a) a surface-protein gene, (b) an insertion site located within the surface-protein gene, and (c) a promoter functionally linked to the expression of the surface-protein gene; and (ii) an insertion sequence, the insertion sequence including a tag moiety sequence physically linked to a foreign nucleic acid.

The insertion sequence of the present invention is formed by physically linking a foreign nucleic acid sequence with a tag moiety sequence, e.g., by ligation. The foreign nucleic acid and the tag moiety may be linked by any well known ligation means, including chemical ligation or enzymatic ligation.

The surface-protein gene of the present invention codes for a protein that is expressed on the surface of the host organism, i.e., some portion of the surface protein is presented to the environment outside the host organism. Exemplary preferred surface proteins include epidermal growth factor, epidermal growth factor receptor, mating factor, and mating factor receptor. When *E. coli* is the host organism, preferred surface proteins include maltoporin (Lam B), K88ac and K88ad pilin proteins, TraT lipoprotein, PhoE and OmpA outer membrane proteins, and the OmpA-lipoprotein fusion protein (Lpp-OpmA), e.g., Georgiou et al., *Trends Biotechnol.*, 11: 6–10 (1993).

The tag moiety sequence may be any sequence which codes for a moiety which is a member of a binding pair, e.g., an antigen, an antibody, a receptor ligand and the like, and which can be inserted into the surface-protein gene without disrupting the expression or localization of the surface protein. Alternatively, the tag moiety sequence may be a sequence which, when inserted into the surface protein gene, causes a change in the expression product of the surface protein gene which results in a change in the binding properties of the host organism, e.g., by altering the reading frame of the surface protein gene.

In an important feature of the present invention, the surface-protein gene includes an internal insertion site for inserting the insertion sequence. Preferably, the insertion site is unique within the vector nucleic acid. When the insertion sequence is inserted at the insertion site, the tag-moiety is expressed at the surface of the host organism. Preferably, the insertion site is located in a part of the surface-protein gene which is expected to be located at the outer surface of the host organism when expressed.

Preferably, the vector nucleic acid further includes a promoter sequence functionally linked to the surface-protein gene for promoting the expression of the surface-protein gene.

Methods utilizing the tag cloning system utilize traditional cloning techniques. First, the vector nucleic acid is cleaved at the insertion site using an appropriate sequence-specific cleaving agent, e.g., restriction endonucleases, under conditions sufficient to render the cleaving agent active. Next, the foreign nucleic acid is ligated to the tag moiety sequence, thereby forming an insertion sequence. The cleaved vector nucleic acid is then contacted with the insertion sequence under conditions sufficient to incorporate the insertion sequence into the vector nucleic acid at the insertion site, e.g., by enzymatic or chemical ligation, thereby forming a recombinant vector nucleic acid. The recombinant vector nucleic acid is then inserted into the host organism by either transfection, transformation, or conjugation, the particular mode of insertion being dependent on the nature of the recombinant vector nucleic acid and the host organism. The host organism is then grown up to provide an opportunity for the expression of the surface-protein gene/tag sequence. Finally, the host organism is contacted with a solid support which has been functionalized with a moiety capable of specifically binding to the tag moiety. If a particular host organism contains a recombinant vector nucleic acid, the host organism will express the tag moiety at its outer surface and will therefore specifically bind to the functionalized solid support.

4. Lethal Gene Inactivation System

In a fourth aspect of the present invention, hereinafter referred to as the "lethal gene inactivation system", the recombination of vector nucleic acid and foreign nucleic acid is linked to the insertional inactivation of a lethal gene in the vector. Note that in this system, recombination is indirectly linked to a SEM or tag molecule through the survival of the host organism. Thus, if the recombination event occurs, the host organism survives, the SEM is expressed, and the surviving host organisms can be isolated using a properly functionalized support as described elsewhere.

Figure 4:
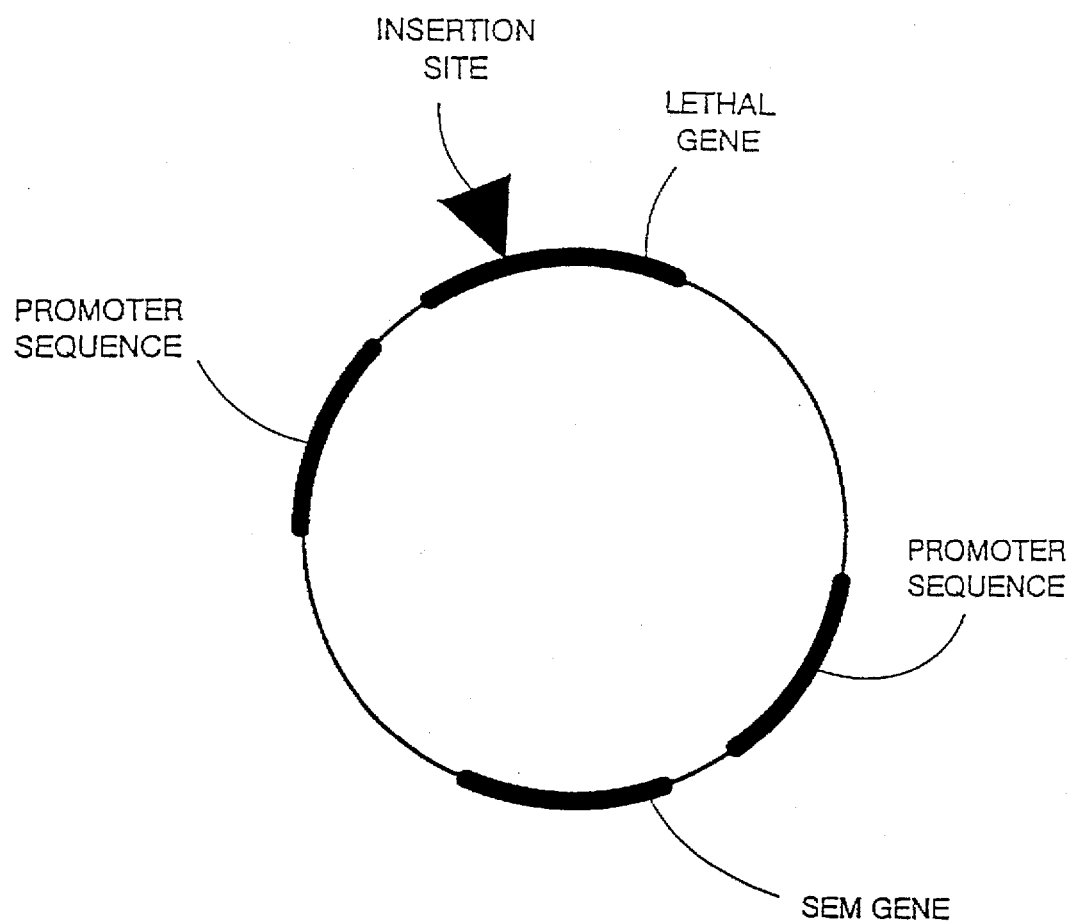
FIG. 4 shows a schematic diagram of the lethal gene inactivation system of the present invention.

As shown in FIG. 4, the lethal gene inactivation system includes a nucleic acid which includes a lethal gene, the expression product of the lethal gene being lethal to a host organism. The nucleic acid of the present system further includes a promoter sequence functionally linked to the lethal gene and an insertion site located within the lethal gene. The insertion site is located such that when foreign nucleic acid is inserted at the insertion site, the lethal gene is insertionally inactivated. Also included in the vector nucleic acid is a surface-expressed-moiety gene, the purpose of which is as described above. In an alternative preferred embodiment, the SEM gene is located on a host nucleic acid.

Preferred lethal genes for *E. coli* include the active cytotoxic ccdB gene under the control of the lacP promoter, e.g., Bernard et al., *Gene*, 148: 71–74 (1994).

Another example of a lethal gene for use in gene inactivation systems is the sacB gene of *B. subtilis*, see Blomfield et al, Mol. Microbiol. 5:1447–1457 (1991).

Methods employing the lethal gene inactivation cloning system utilize cloning techniques well known in the art of molecular biology. First, the nucleic acid of the invention is cleaved at the insertion site using an appropriate cleaving agent or combination of cleaving agents under reaction conditions sufficient to render all the cleaving agents active. The cleaved nucleic acid is then contacted with a foreign nucleic acid under conditions sufficient to incorporate the foreign nucleic acid into the nucleic acid at the insertion site, e.g., by enzymatic ligation, thereby forming a recombinant nucleic acid. The recombinant nucleic acid is then inserted into the host organism by either transfection, transformation, or conjugation, the particular mode of insertion being dependent on the nature of the recombinant vector nucleic acid and the host organism. The host organism is then grown up to provide an opportunity for the expression of the lethal gene and the surface-expressed moiety. Finally, the host organism is contacted with a solid support which has been functionalized with a moiety capable of specifically binding to the SEM (see below). If a particular host organism contains a recombinant nucleic acid, the host organism will survive to express a SEM at its outer surface and will therefore bind to the functionalized solid support.

5. Host Capture System

The host capture system of the present invention provides a means for isolating a host organism which has been transformed with recombinant nucleic acid using any of the cloning systems described above. Generally, the host capture system includes a plurality of binding moieties which are attached to a solid support. The binding moieties are members of a binding pair the complementary member of which is differentially expressed on the surface of a host organism, e.g., a SEM, or tag moiety. Although the majority of embodiments and examples described herein are used in conjunction with the isolation of recombinant cells, the host capture system may be used to isolate non-recombinant single cells of interest that express binding moieties of interest on their surface, e.g., the isolation of a subpopulation of T lymphocytes having T cell receptors for an antigen of interest.

Preferably, the binding pair should have an equilibrium dissociation constant ($K_d$) which is in the micromolar or submicromolar range, where, as used herein, the term equilibrium dissociation constant refers to the ratio of unbound to bound binding moieties at equilibrium expressed in concentration units. A dissociation constant in this range facilitates the efficient capture of the recombinant host organisms and provides the requisite selectivity between specifically bound and non-specifically bound host organisms. More preferably, at least one member of the binding pair includes a reactive functional group enabling it to be covalently immobilized to a solid substrate, or to a linker attached to a solid substrate.

Preferably, the binding moiety that is differentially expressed at the surface of the host is chosen such that overexpression of that moiety in the host organism is possible without compromising the viability of the host organism Such overexpression provides a multiplicity of possible binding sites for binding to the functionalized solid support.

The choice of a particular binding pair is a strong function of the host organism being used. Such binding pairs may be chosen generally among ligand/receptor pairs, antigen/ antibody pairs, biotin/avidin pairs, metalchelator pairs, carbohydrate/ lectin pairs, and any other like binding pairs.

One preferred binding pair useful in cases where *E. coli* is used as the host organism is based on the outer membrane receptor protein FhuA. The FhuA protein binds specifically to a ferrichrome class of siderophores, where as used herein, the term "siderophore" refers to a low-molecular weight iron(III) transport agent produced and utilized by many aerobic microorganisms, e.g., H. Nikaido, *Trends Microbiol.*, 1: 5–7 (1993), and V. Braun, *Trends Biochem. Sci.*, 10: 75–78 (1985). A preferred ferrichrome class siderophore is ferricrocin, e.g., M. Llinas and J. B. Neilands, *Bioinorg. Chem.*, 2: 159–165 (1972).

A particularly preferred binding pair useful in *E. coli*-based systems relies on the interaction of type 1 fimbriae of *E. coli* and bovine ribonuclease B (RNAse B). Most*E. coli* K-12 strains contain ca. 100–300 type 1 fimbriae at the cell surface, each fimbria having a width of ca. 7 nm and a length of 0.2 to 2 pm, and are present at many sites around the cell. These fimbriae are adhesive organelles important for successful bacterial recognition and colonization of specific host tissues. A single fimbria consists of ca. 1,000 repeating subunits of mostly a single polypeptide (FimA) having a molecular mass of ca. 17 kilodaltons (kDa). The minor subunit (Fimi mediates specific binding to D-mannosyl residues e.g., Klemm, P., and Krogfelt, K. A. in P. Klemm (ed.), *Fimbriae, Adhesion, Genetics, Biogenesis and Vaccines*, p 9–26, CRC Press, Boca Raton, Fla. (1994). The fact that type 1 fimbriae exhibit high affinity for D-mannosyl residues suggested the use of bovine ribonuclease B as the complementary member of the binding pair. Bovine ribonuclease B is a glycoprotein with a molecular mass of 15.5 kDa which consists of 124 amino acids with a unique glycosylation site including five glycoforms with oligosaccharides of five to nine mannose residues, e.g., D. Fu, L. Chen, and R. A. O'Neill *Carbohydr. Res.* 261: 173–186 (1994). The well known ability of RNAse B to stick to hydrophobic substrates such as glass and polystyrene suggested that suitably patterned substrates with adsorbed RNAse B could be used to capture single *E. coli* cells (1×3 µm). It will be appreciated by those skilled in the art, that mannose containing glycoproteins in addition to ribonuclease B, as well as mannosyl containing carbohydrates, may be used to bind type 1 fimbriae (or other mannose binding proteins).

Additional preferred binding pairs useful in systems using *E. coli* as the host organism include the cell surface determinants flagella/antiflagellin protein, e.g., Macnab, *Annu. Rev. Genet.*, 26: 131–158 (1992) and Silverman et al., *Nature*, 249: 73–74 (1974); fimbriae/antifimbriae protein or cognate receptors, e.g., Ofek et al., *Curr. Top. Microbiol. Immunol.*, 151: 91–113 (1990), and Gbarah et al., *Infect. Immun.*, 59: 4524–4530 (1991), and Klemm et al., *Mol. Microbiol.*, 4: 553–559 (1990), and Nilsson et al., *Bio/ Technology*, 12: 1376–78 (1994); and lipopolysaccharide (LPS)/anti-LPS protein.

Yet another preferred binding pair system useful in systems using *E. coli* as the host organism is the outer membrane receptor protein BtuB which selectively binds the vitamin B12 class of molecules, e.g., Holroyd et al., in Leive et al. (eds.), *Microbiology*-1994, p.21–23, American Society for Microbiology, Washington, D.C. (1994).

For gram positive host organisms, preferred binding pairs include the membrane receptor protein FhuD of Bacillus subtilis which binds members of the ferrichrome family of siderophores including ferricrocin, e.g., Schneider et al., *Mol. Microbiol.* 8: 111–121 (1993).

For systems using yeast as a host organism, a preferred binding pair is the membrane α-factor pheromone receptor (Ste2) of the yeast *Saccharomyces cerevisiae* which binds to the mating α factor, e.g., Kurjan, *Annu. Rev. Biochem.* 61: 1097–1129 (1992).

For systems utilizing mammalian host organisms, preferred binding pairs include the epidermal growth factor/ epidermal growth factor receptor pair and the bombesini-bombesin receptor pair, e.g., Fantl et al., *Annu. Rev. Biochem.*, 62: 453–481 (1993) and Spindel et al., *Recent Prog. Honn. Res.* 48: 365–391 (1993). Another preferred embodiment for capture of transiently transfected mammalian cells is based upon binding to the hapten , 2-phenyl-5-oxazolone, to a single chain antibody (scFv), as described in J. D, Chestnut et al , *J. Immunol. Methods*, (1996).

The solid supports used to immobilize one of the binding moieties are preferably flat, chemically well defined, i.e., chemically homogeneous, not water soluble, capable of chemical modification, and wettable by an aqueous solvent. Preferred materials include glass, quartz, silicon, plastic (such as polystyrene, polyethylene, polypropylene, etc.), metal, and the like.

In a preferred embodiment of the present invention, the immobilized binding moiety is attached to the solid support at a plurality of discrete anchor sites, where, as used herein, the term "anchor site" refers to a location on the solid substrate having one or more binding moieties attached thereto such that there is an essentially binding-moiety-free region separating each anchor site. Such attachment may be based on covalent attachment or physical adsorption, e.g., hydrophobic adsorption or charged-based adsorption. The solid substrate comprising one or more binding moieties is referred to herein as an "anchor site array." Preferably, each anchor site has dimensions such that only a single host organism can bind to a single anchor site. When *E. coli* is the host organism, and single cells are to be isolated, preferably each anchor site should have an area of approximately 1 square micrometer. The dimensions of the anchor site necessary to bind a single cell will vary with respect to the size of the cells of interest. Generally, larger sizes may be used to bind larger cells. Given that the sizes of most cells are known, the dimensions of an anchor site suitable to bind a single cell may readily be determined.

In a more preferred embodiment, the anchor sites are arranged in a high density regular array. By arranging the anchor sites in such a way, the location of each bound host organism can be uniquely determined.

One preferred method of forming an ordered array of covalently immobilized moieties is by using linking groups, where, as used herein, the term "lining group" refers to a chemical species which serves to link a binding moiety to a solid support. Preferred linker molecules have both aqueous and membrane solubility. Particularly preferred linking groups include homopolymers of ω-aminopolyethyleneglycol (PEG) carboxylic acids or (ω-aminoalkanoic acids such as ε-aminocaproic acid.

A particularly preferred method of forming a high-density array uses long-chain alkanethiols as linking groups, i.e., molecules having the formula $HS(CH_2)_nX$, where n is preferably greater than 10, and X is an attachment group which facilitates covalent attachment of the binding moiety to the linking group. Long-chain alkanethiols rapidly form ordered, oriented, self-assembled monolayers on evaporated gold films deposited on glass substrates with the attachment group X facing away from the solid support. High resolution patterns of self-assembled monolayers (SAM) of alkanethiolates on gold substrates can be readily fabricated with dimensions as small as 1 µm, e.g., Kumar et al., *J. Amer. Chem. Soc.* 114:9188–9189 (1992). The dimension of the SAM at each array location or anchor site should not be larger than the projected area of a host organism to ensure that only a single host organism is captured at each location.

An alternative method for forming a high density array utilizes photolithography techniques. In this method, the surface of the solid substrate is treated with an agent that facilitates attachment of a binding moiety, e.g., an organosilane. The substrate is then treated with a photoresist agent to form a layer of photoresist material and baked to cure the photoresist. Next, the surface is exposed with ultraviolet light through a mask having a desired pattern, the mask defining the pattern of the array. The exposed substrate is then developed with developing agent removing either the exposed regions of photoresist, i.e., a positive photoresist, or the masked regions of photoresist, i.e., a negative photoresist. The steps of exposing and developing create regions of masked and unmasked surface. The substrate is then contacted with a solution of binding moiety, the binding moiety attaching to the substrate only at locations not coated with the photoresist, i.e, unmasked surface. Finally, the remaining photoresist is removed, resulting in a surface patterned with zones of binding moiety.

The host organism capture systems of the invention may be adapted for carrying out numerous molecular biology processes in addition to the capture of single cells at the anchor sites. Such processes include cell growth, ordered host cell library formation, polynucleotide capture, polynucleotide amplification, capture of polynucleotide amplification products, DNA sequencing, and the like. By combining one or more of such processes with single cell capture, the host organism capture systems of the invention may be used to reduce the number of manipulations required for the analysis of isolated single cells. Furthermore, embodiments of the subject host organism capture systems designed for carrying out one or more of the indicated molecular biology processes may readily be used in conjunction with automated apparatus, thereby providing for even greater convenience and times savings.

In one embodiment, host organism capture systems comprise an anchor site array 5 and a plurality of incubation chambers 50. The incubation chambers 50 are in register with the anchor sites 10. Each incubation site 10 comprises an input port 25, an output port 35, and chamber walls 30. Generally, the chamber walls 30 form the input ports 25 and output ports 35. The input ports 25 and output ports 35 may take the form of openings in the incubation chambers 50. Preferably, the input ports 25 and the output ports 35 are at opposite ends of the incubation chambers 50. For example, an incubation chamber 50 may take the form of a cylinder, wherein the one end of the cylinder is designated the input port 25 and the other end of the cylinder, i.e., the end proximal to the anchor site 10, is designated the output port 35. Each output port 35 (and hence each incubation chamber 50) surrounds a single anchor site 10 on the anchor site array 5. The incubation chambers enclose the anchor sites 10 in a liquid occlusive manner. In other words, liquid introduced into an incubation chamber 50 (through an input port 25) will not enter a second incubation chamber 50. Thus liquid introduced into an incubation chamber 50 (through an input port 25) will contact a single anchor site 10 (through the output port 35), but will not contact any other anchor site 10.

The incubation chamber may be formed by an adaptor plate 20 (FIGS. 9–12). The adaptor plates 20 comprise a plurality of incubation chambers 50 in an array. The input and output ports of the incubation chambers 50 are formed by the chamber walls 30. The incubation chambers 50 of the adaptor plate 20 are in a configuration that places them in register with the anchor sites 10 on the anchor site array 5.

The host organism capture systems may comprise a sealing gasket 15 located between the anchor site array and the output ports. The sealing gasket serves to provide a liquid occlusive seal between the incubation chambers. The sealing gasket comprises an opening or openings 55 for the flow of liquid between the output port 35 and the anchor site 10. In place of, or in addition to, a sealing gasket 15, a liquid occlusive seal between the adaptor plate 20 and the anchor site array 5 may be achieved through an adhesive layer connecting the two components.

Figure 8:
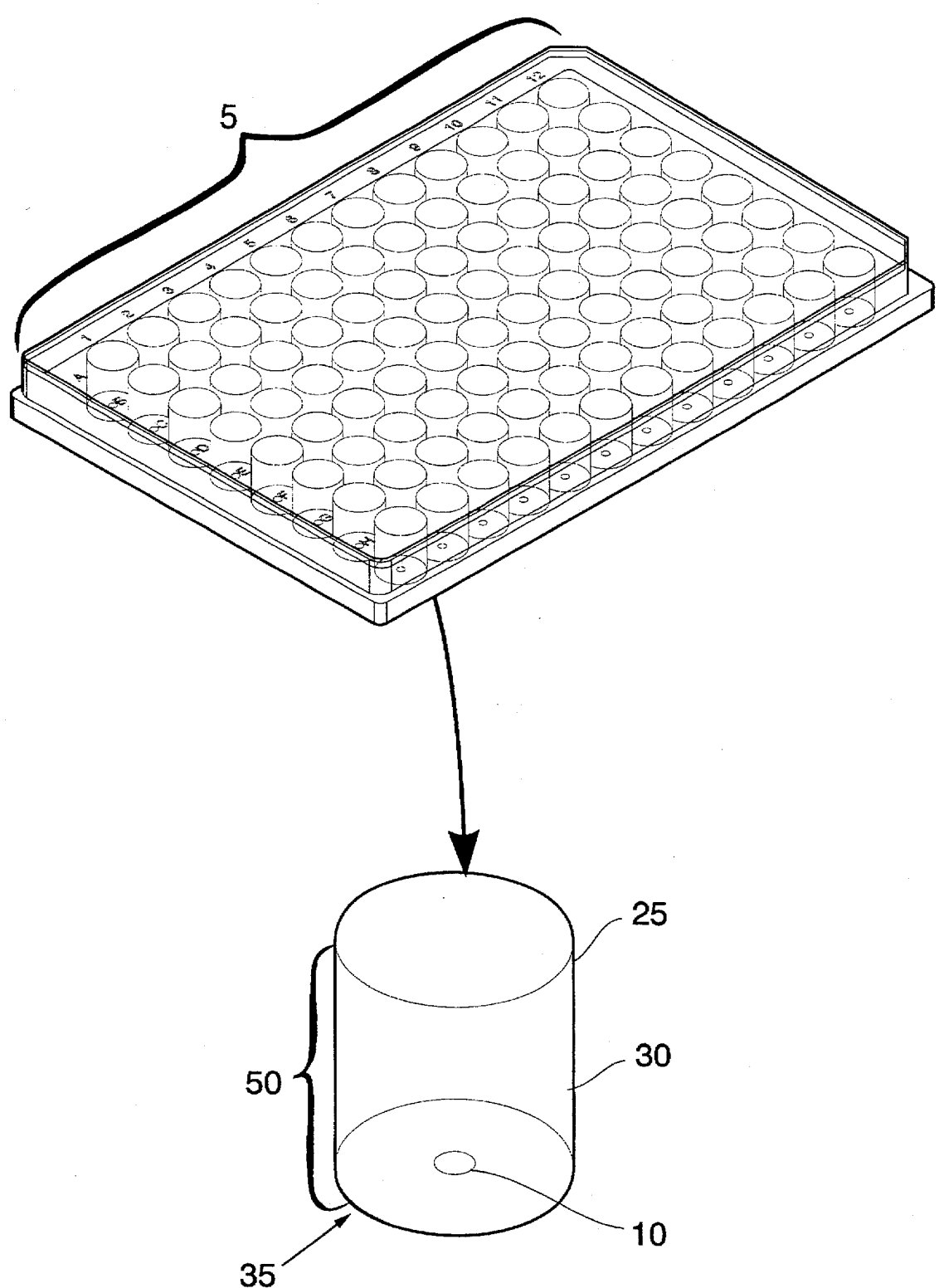
FIG. 8 is a perspective view of a host cell capture device in which the incubation chambers 50 are formed from the same solid support unit that forms the anchor site array 5. A detailed view of an incubation chamber is shown.
Figure 9:
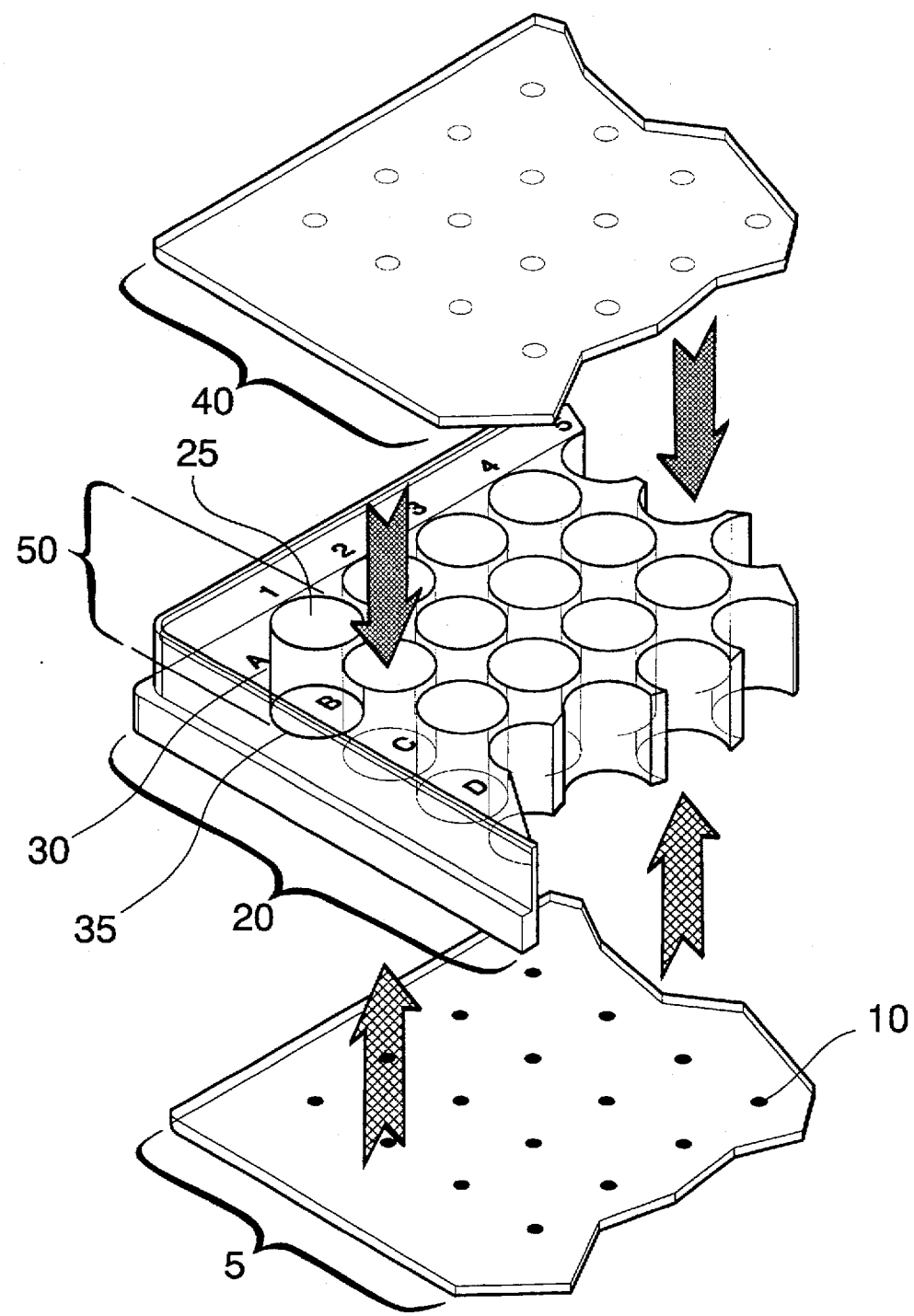
FIG. 9 is an exploded perspective view of an embodiment of a host cell capture device comprising a anchor site array 5, an adaptor plate 20, and a cover plate 40.
Figure 10:
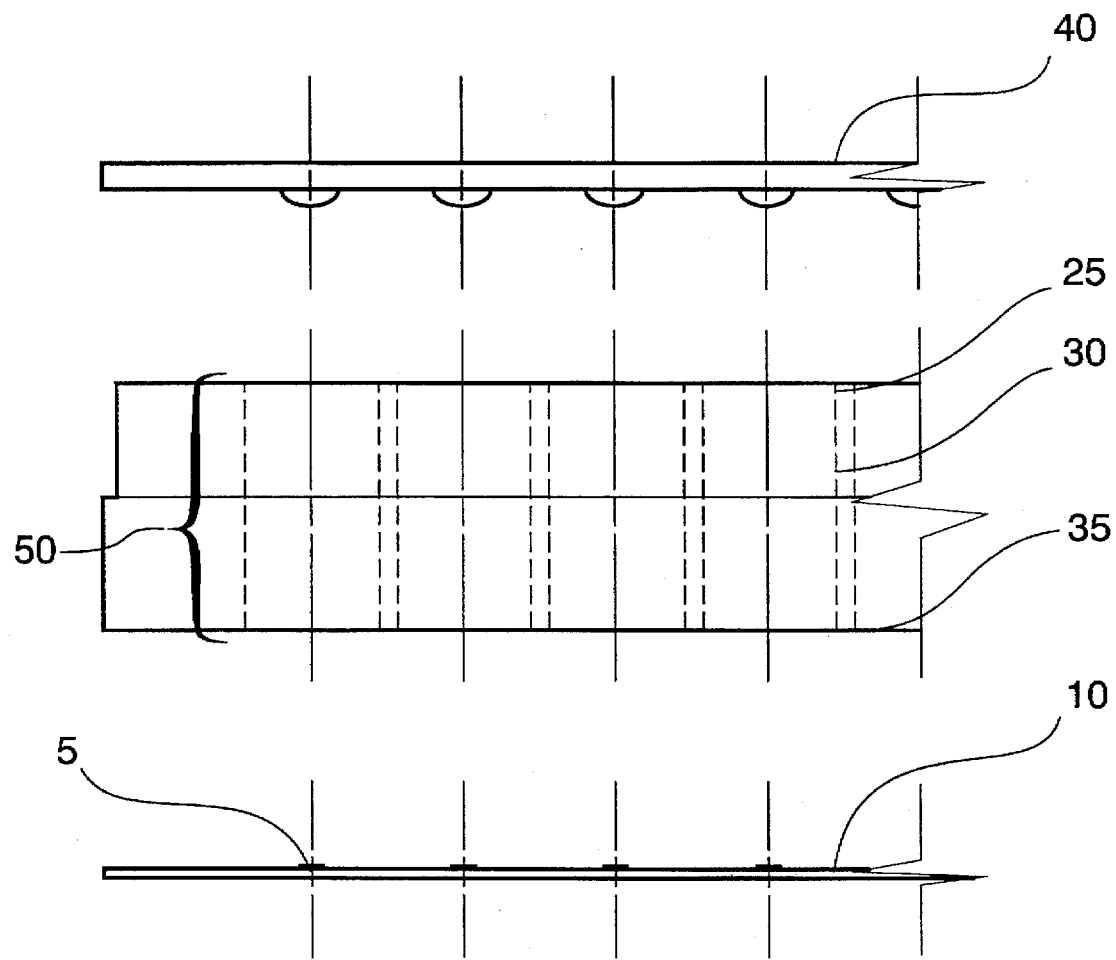
FIG. 10 is an end view of the embodiment of the host cell capture device shown in FIG. 19.
Figure 11:
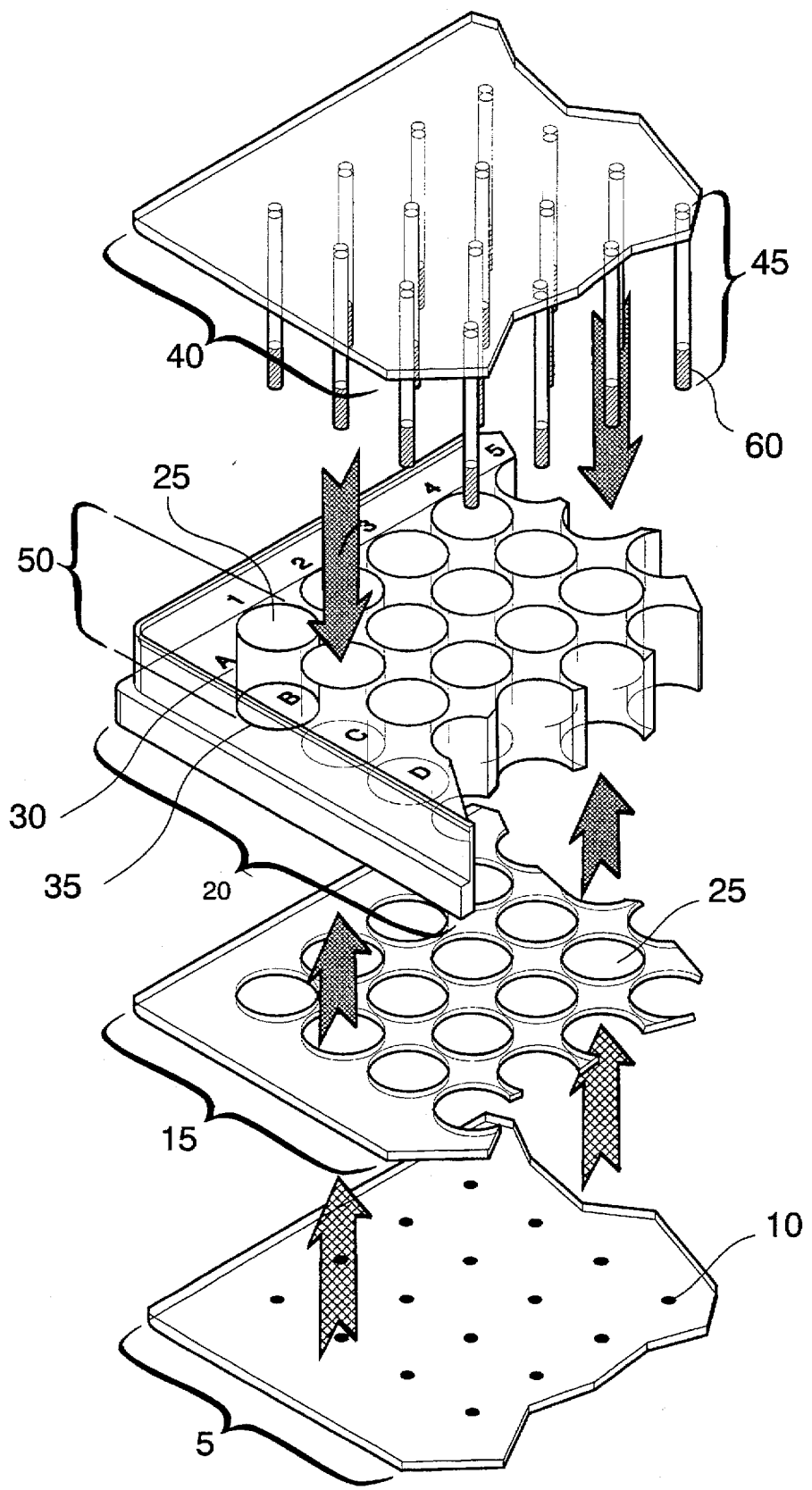
FIG. 11 is an exploded perspective view of a host cell capture device comprising a anchor site array 5, an adaptor plate 20, a sealing gasket 15, and a cover plate 40. The cover plate 40 has projection members 45 that may optionally comprise capture regions.
Figure 12:
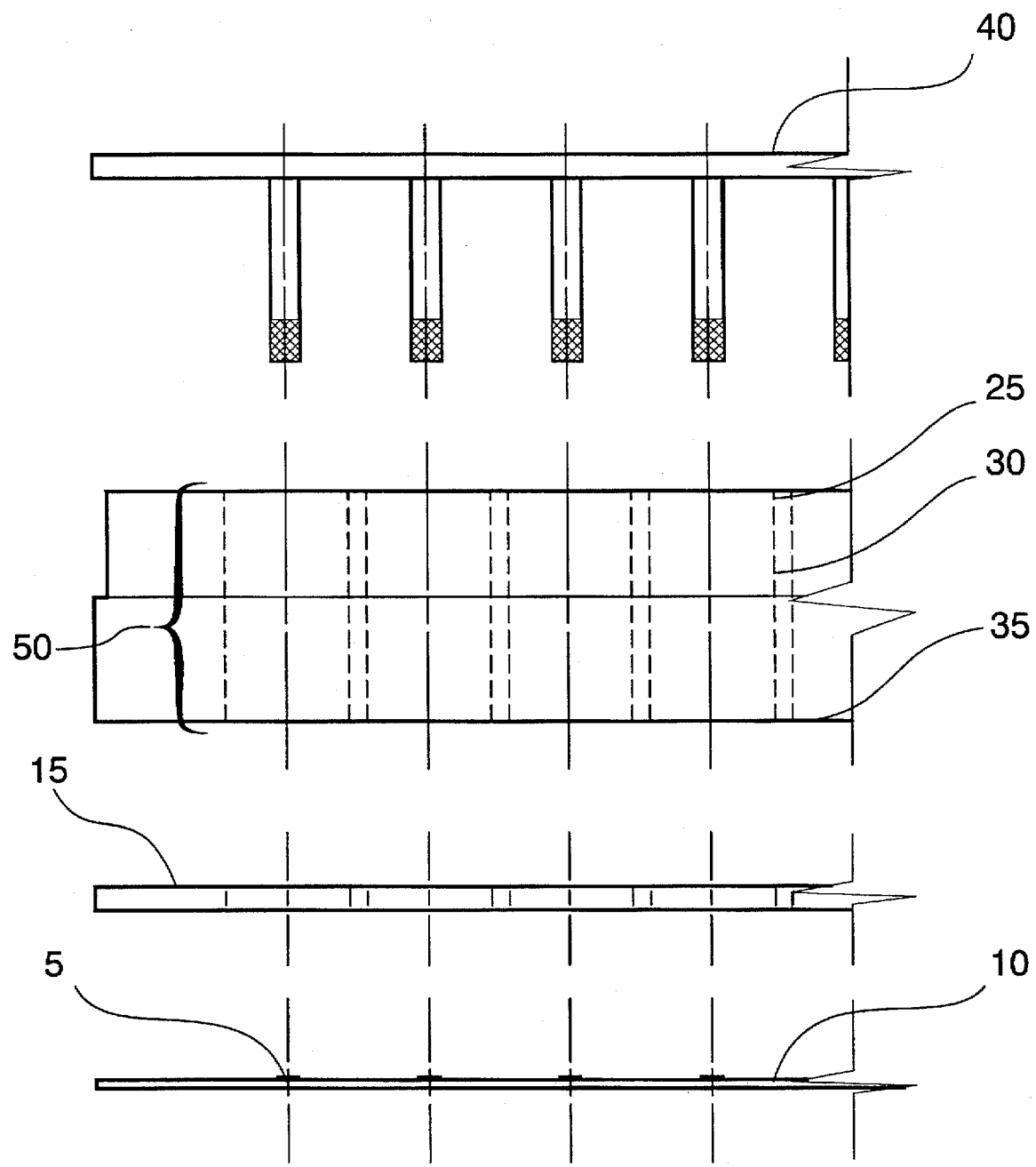
FIG. 12 is an end view of the embodiment of the host cell capture device shown in FIG. 21.
Figure 13:
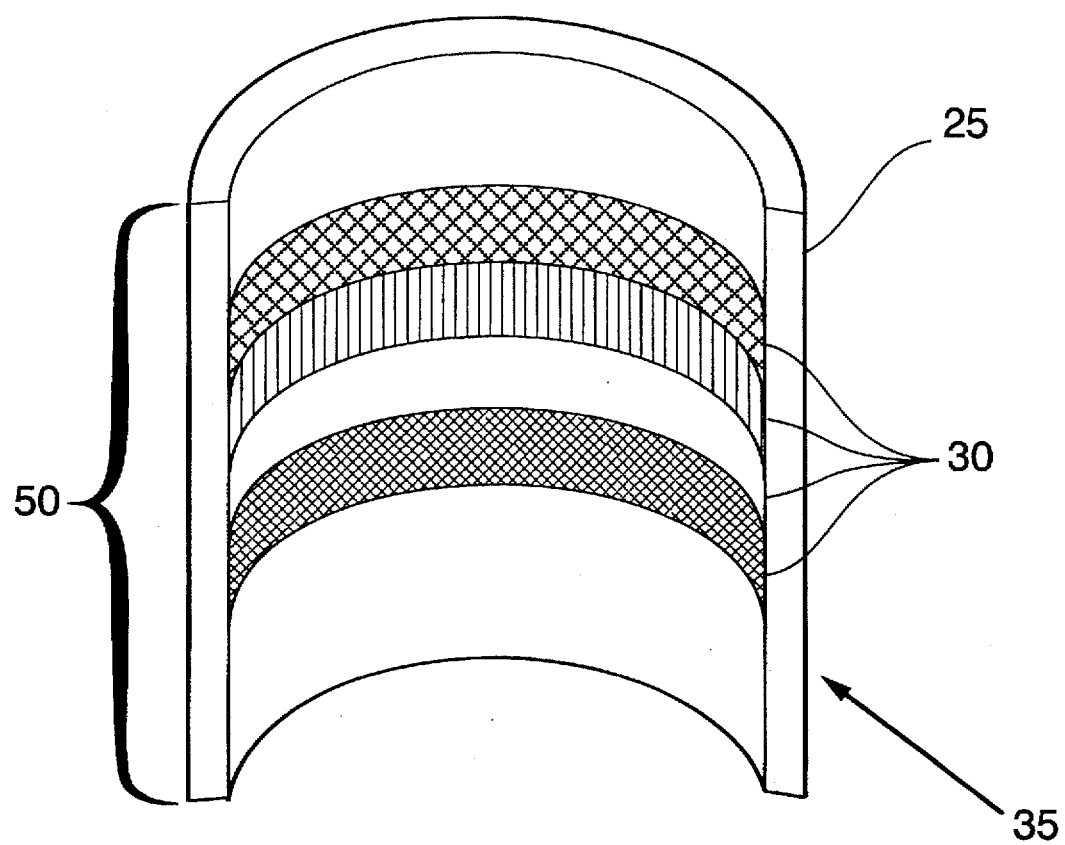
FIG. 13 is a cross section of an incubation chamber 50 having four different capture regions 60.

In some embodiments of the invention [FIG. 8], the incubation chambers may be formed from the solid support that is part of the anchor site array 5. In such embodiments, the walls of the incubation chambers 50 are formed directly from the solid support. Similarly, the input ports 25 and output ports 35 are also formed from the solid support. An example of a configuration of the host cell capture device in which the incubation chambers are formed from the solid support may be visualized as a microtiter plate in which an anchor site 10 is present at the bottom of each well.

In additional embodiments of the invention, the host organism capture system further comprises a cover plate 40. The cover plate 40 is generally of about the same size and dimensions of the device comprising an anchor site array 5 and a plurality of incubation chambers 50. The cover plates 40 have a top and bottom surface. The bottom surface of the cover plate is positioned so at to face, i.e., oppose, the input ports 25 of the incubation chambers 50.

The host organism capture systems may comprise a sealing gasket located between the cover plate 40 and the input ports 25. The sealing gasket serves to provide a liquid occlusive seal between the incubation chambers. The sealing gasket comprises an opening or openings for the flow of liquid between the input ports 25 and the cover plate 40. In place of, or in addition to, a sealing gasket, a liquid occlusive seal between the adaptor plate and the cover plate. Anchor site array 5 may be achieved through an adhesive layer joining the adaptor plate 20 and the cover plate 40.

Embodiments of the host organism capture system further may comprise one or more capture regions 60 for each incubation chamber unit. The term "incubation chamber unit" is used to indicate a portion of the host organism capture system that consist of a single incubation chamber 50, the portion of the anchor site array 5 surrounded by the output port of the incubation chamber, and any region of a cover plate 40 (optionally present) surrounded by the input port 25 of the incubation chamber 50. Capture regions 60 are discrete portions of an incubation chamber unit that comprises a moiety that is member of a specific binding pair and is immobilized at one or more site on each incubation chamber unit. Capture regions 60 may be cell capture regions, non-specific polynucleotide capture regions, or sequence-specific polynucleotide capture regions, as determined by the specific binding moiety selected for the capture region 60.

Cell capture regions are capture regions 60 designed for the binding of binding moieties that are differentially expressed on the surface cells of interest. Preferably, the binding moieties of the cell capture regions are the same as the binding moieties of the anchor sites 10. The binding moieties of the cell capture regions may be immobilized by the same methods used to immobilize binding moieties to anchor sites 10. Cell capture regions are at least the same size, and preferably larger than anchor sites 10. Capture regions 60 that are larger than anchor sites 10 may be used to bind a plurality of cells differentially expressing the moiety of interest, whereas anchor regions 10 are designed to capture single cells. In a preferred embodiment of the invention, the host cell capture region comprises a plurality of cell capture regions, each region located on the bottom surface of a cover plate 40 and in register with the anchor sites 5. Cell capture regions may also be located on the chamber walls 30 of the incubation chambers 50.

Non-specific polynucleotide capture regions are capture regions 60 in which the immobilized binding moiety is a non-specific polynucleotide binding reagent. Non-specific polynucleotide binding reagents are compounds that bind DNA or RNA in a non-sequence specific manner. Examples of non-specific polynucleotide binding reagents include silica, glass milk, polynucleotide intercalating compounds, nitrocellulose, organic compounds with free carboxyl groups, DEAE groups, anionpolynuclers, polynucleotides, and synthetic polynucleotide derivatives. Non-specific polynucleotide binding reagents may be immobilized to solid supports using conventional immobilization techniques such as those described in G. T. Hermanson et al, *Immobilized Affinity Ligand Chromatography*, Academic Press, San Diego (1992). The non-specific polynucleotide capture regions may be at a variety of locations with a given incubation chamber unit. In one embodiment of the invention, the anchor site arrays comprise a plurality of non-specific polynucleotide capture regions, wherein each non-specific polynucleotide capture region is located in close proximity to an anchor region so as to provide for the binding of polynucleotides released from a cell bound to a given capture region.

Sequence-specific polynucleotide capture regions comprise a sequence-specific polynucleotide binding reagent as the immobilized binding moiety of the capture region 60. Sequence-specific polynucleotide binding reagents are compounds that bind DNA or RNA in a sequence- specific manner. Generally, sequence-specific polynucleotide binding reagents are polynucleotides or synthetic analogs of naturally-occurring polynucleotide that comprise a base sequence that is complementary to the base sequence of the polynucleotide of interest. Examples of sequence-specific polynucleotide binding reagents include DNA, RNA, phosphorothioate, phosphorarnidates, peptide-nucleic acids (PNAs), methylphosphonates, and the like. Sequence-specific polynucleotide binding reagents may be immobilized to solid supports using conventional immobilization techniques such as those described in Nunc Tech Note. vol 3, No. 16, G. T. Hermanson, *Bioconjugate Techniques*, Academic Press, San Diego (1996), as well as numerous reference on polynucleotide synthesis. The sequence-specific polynucleotide capture regions may be at a variety of locations with a given incubation chamber unit. The polynucleotide (or synthetic derivatives thereof) used for sequence specific capture may be used to prime reactions such as sequencing reactions, PCR amplification, and the like, from the captured polynucleotides.

The bottom surface of the cover plate 40 may optionally comprise a plurality of projection members 45. The projection members are in register with the incubation chambers 50. The projection members may extent into the incubation chambers. One or more of the projection members 45 my extend into a single incubation chamber 50. Capture regions 60 may be present on the on the projection members.

Other aspects of the invention include methods of analyzing individual cells of interest. The subject methods employ host organism capture systems of the invention. The method involve the capture of single cells that are differentially expressing a binding moiety on their surface. The captured single cells (or the polynucleotides of interest within The capture cells may be analyzed by the subject methods).

The methods comprise the step of contacting a liquid containing a cell population with an anchor site array, i.e., a solid support comprising a plurality of binding moieties attached to a solid support, the binding moieties being members of binding pairs, the complementary member of the binding pair being differentially expressed on the surface of the cell of interest. Single cells surface expressing the binding moiety are bound to individual anchor sites 10. The contacting step typically involves immersing or rinsing an anchor site array 5 in a liquid comprising a cell population of interest so that the cells contact one or more anchor sites. A portion of the cell population of interest differentially expresses a surface expressed binding moiety. One example of a suitable population of cells is a population of cells transformed by the surface-expressed-moiety gene vector cloning system of the invention, wherein the liquid employed is cell growth medium. After the contacting step, the anchor site array 5 is preferably washed so as to remove cells that have not bound to the anchor sites 10.

Cells that have been bound to individual anchor sites 10 may then be lysed to release polynucleotides. Methods for lysing cells so as to release polynucleotide are well known to persons of ordinary skill in the art of molecular biology. Lysis methods include exposure of cells to lysozyme, detergent, and the like. The range of choices of lysis methods will be dictated by the type of cells to be analyzed. Preferably, lysis takes place in the incubation chambers.

Lysis results in the release of polynucleotides from the bound individual cells. The released nucleic acid may be analyzed in variety of ways. The released polynucleotide may bind to non-specific polynucleotide capture regions or sequence-specific polynucleotide capture regions present in individual incubation chamber units on the host cell capture device. The conditions in the incubation chambers may be adjusted so as to provide for the desired binding. Conditions that may be used to control binding include temperature, ion concentration, and the like.

The binding of polynucleotides released from captured cells to either sequence-specific or non-sequence specific capture regions may be used to purify the polynucleotide away from contaminating compounds that might interfere with subsequent analysis. Host cell organism capture systems having polynucleotides bound at one or more capture regions may be washed repeatedly so as to remove contaminating compounds.

Polynucleotides that have been bound to sequence-specific or non-specific capture regions may be subsequently characterized using well known biochemical analysis techniques. Optionally, the bound polynucleotides may be released prior to performing the analytical techniques. The biochemical technique may be carried out in parallel in the different incubation chambers of the host cell capture system. For example, a nucleic acid amplification technique such as the polymerase chain reaction (PCR) may be use to amplify a subset of the bound polynucleotides. Detailed descriptions of how to perform PCR and related amplification techniques can be found in The Polymerase Chain Reaction, Mullis ed., Springer-Verlag, NY, N.Y. (1994), PCR A *Practical Approach Volume* 2, McPherson ed., IRL Press, Oxford (1995). Another example of a biochemical technique that may be performed on bound polynucleotides is polynucleotide sequencing. Detailed descriptions of techniques for polynucleotide sequencing can be found in *Nucleic Acid Sequencing: A Practical Approach Volume* 2, Howe and Ward eds., IRL Press, Oxford (1989). Another example of biochemical analytical techniques that can be performed on polynucleotides bound to capture regions is nucleic acid hybridization to labeled hybridization probes. Detailed descriptions of techniques for nucleic acid hybridization can be found in *Molecular Cloning A Laboratory Manual*, Sambrook et al, ColdSpring Harbor Press, Cold Spring Harbor, N.Y. (1989).

In another embodiment of the subject methods of analyzing individual cells of interest, the method further comprises the step propagating the individual cells that are bound to the anchor site 10 on the anchor site arrays 5. The bound cells may be propagated by adding suitable growth medium to the incubation chambers 50 and incubating the host cell capture device at suitable temperature for a period of time sufficient to produce the desires amount of progeny cells. The progeny cells may then be bound at secondary cell capture sites located on the bottom surface of the cover plate 40 or located on the chamber walls 30.

The captured progeny cells that are produced by the single cells bound to the anchor site may be lysed and the released polynucleotides subjected to biochemical analysis as described above e.g., PCR, sequencing, hybridization, and the like. Additionally, a portion of the host organism capture system comprising bound progeny cells may be removed and set aside for storage, i.e, archiving. Preserving agents such as glycerol or DMSO may be added so as to provide for storage at reduced temperatures. For example, a cover plate comprising cell capture regions that have been bound to progeny cells may be removed from the host organism capture system. The cover plate 40 may then be stored and used as a source of host cells containing the polynucleotide of interest. Thus, for example, after DNA from a DNA capture site in a given incubation chamber 50 had been isolated and sequenced, host cells containing the desired polynucleotide sequence could be recovered from the cover plate by finding the cell capture site that corresponds to the incubation chamber 50 comprising the DNA sequence of interest. By combining the steps of ordered library creation and polynucleotide analysis, great savings in time and expense may be realized.

In another embodiment of the subject method, additional biochemical analytical steps may be performed after the host cell archiving step. For example, the progeny cells may be bound to cell capture regions located on the walls of the incubation chambers 50. After the bound cells may then be lysed and the released polynucleotides bound to non-specific polynucleotide capture regions, e.g., immobilized silica particles, the bound polynucleotide may then be washed so as to remove contaminants. The sequencing chambers having the bound polynucleotides may then be archived. Alternatively, after washing, PCR amplification primers, a DNA polymerase, and other reagents necessary for PCR may be added to the incubation chambers. The incubation chambers may then be subjected to a series of thermocycles in order to amplify a DNA sequence of interest. The amplified DNA may then be bound on sequence specific polynucleotide capture regions, e.g., immobilized sequencing primers. Polynucleotide sequencing reagents such as dye-labeled terminators, dNTPs, DNA polymerase, and the like may then be added to the incubation chambers in order to provide for sequencing of the bound polynucleotide sequences of interest.

6. Examples

The invention will be further clarified by a consideration of the following examples, which are intended to be purely exemplary of the invention and not to limit the scope of the invention.

EXAMPLE 1

Binding of fimbriated *E. coli* to polystyrene/glass slides previously adsorbed with RNAse B Slides were functionalized with RNAse B by adding 10–20 µl of RNAse B (0.5–500 µg/ml) in 0.1M Tris, pH 8.3 buffer, and placing slides at 4° C. for 16 h in a water saturated chamber. Slides were then rinsed first with PBS, 0.1% Tween 20, 0.1 mM EDTA, followed with sterile water before incubation with *E. coli*. Strains were grown in LB medium at 37° C. until log phase, washed with PBS, 1% BSA, 0.1 mM EDTA, and resuspended in one-half of the original volume of the culture in the same buffer.

RNAse B-adsorbed substrates were incubated with bacterial suspension for 40 min at room temp, then washed gently several times with cold PBS, 0.1% Tween 20, 0.1 mM EDTA. Substrates were viewed by light microscopy. *Escherichia coli* AAEC356 (M. S. McClain, I. C. Blomfield, K. J. Eberhardt, and B. I. Eisenstein *J. Bacteriol.* 17:4335–4344 (1993)), expressing type 1 fimbriae, bound confluently to areas of glass microscope slides, previously adsorbed with RNAse B. See FIG. 5. Conversely, no binding of *E. coli* AAEC072 (I. C. Blomfield, M. S. McClain, and B. I. Eisenstein, *MoL Microbiol.* 5:1439–1445 (1991)), an isogenic non-fimbriated strain, was observed with RNAse B-adsorbed glass sides. Similar results were observed with RNAse B adsorbed on polystyrene microscope slides (data not shown).

These results demonstrate that *E. coli*, expressing type 1 fimbriae, can be specifically captured on substrates previously adsorbed with RNAse B. Non-fimbriated *E. coli* are not captured.

EXAMPLE 2

Patterning of Silanized Quartz Substrates with RNAse B

In order to capture single *E. coli* cells expressing type 1 fimbriae, it is necessary to adsorb RNAse B to discrete areas of a substrate. This adsorption was accomplished by microlithography as follows.

Four-inch diameter quartz wafers were silanized with octadecyltrichlorosilane to increase the hydrophobicity of the surface. This treatment increased the ability of the substrate to adsorb RNAse B. The silanization procedure was as follows. Wafers were "puddled" with 10% octadecyltrichlorosilane in toluene and then spun to fully coat the wafers. This procedure was repeated three times. Wafers were then "puddled" with toluene and spun to remove unreacted silane. This procedure was repeated several times. Wafers were then "puddled" with isopropanol and spun, "puddled" with 90% isopropanol-water and spun, and finally "puddled" with water and spun several times. Wafers were cured at 110° C. for 15 min.

The silanized quartz wafers were then puddled with Shipley microposit S1813 photoresist (Marlborough, MASS.) and then spun. The resulting wafers were soft baked at 90° C. for 30 min.

A mask (designated mask 1) containing arrays of 50 µm, 25 µm, 10 µm, 5 µm, 2.5 µm, 1.0 µm, 0.75 µm, and 0.5 µm squares was constructed. Within a given size array, squares were separated by 100 µm, i.e., the array had a pitch of 100 µm. A second mask (designated mask 2) consisting of lettering was also used. Following exposure of ultraviolet light through the masks for 8 sec, the wafers were developed with Shipley microposit MF-319 for 30 sec in the dark.

Each photoresist-patterned wafer was treated with 40 ml of 100 µg/ml RNAse B in 0.1M Tris, pH 8.3 buffer, at 4° C. for 16 h. Wafers were washed first with PBS, 0.1% Tween 20, 0.1 mM EDTA, then with sterile water. These wafers were then allowed to dry at ambient temperature.

Photoresist from the above wafers was removed by stripping with acetone for 20 seconds at room temp, followed by rinsing with fresh acetone. The resulting wafers contained RNAse B adsorbed only within the squares from the mask.

EXAMPLE 3

Capture of single *E. coli* K-12 Cells Expressing Type 1 Fimbriae to RNAse B-Adsorbed Silanized Quartz Fimbriated strain AAEC356 was grown and washed as described above in Example 1. RNAse B-adsorbed silanized quartz wafers prepared as in Example 2 were incubated with bacterial suspension as described above. Wafers were viewed by light microscopy.

For wafers generated with mask 2, lettering formed with confluent fimbriated *E. coli* bacteria resulted. For wafers generated with mask 1 consisting of arrays of different-sized squares, confluent cells were observed within the 50, 25, and 10 µm squares. Two or three cells were observed within the 5 µm squares. See FIG. 11. A single cell was captured within virtually every 2.5 m square, i.e., 24 of 25 shown in FIG. 12. No cells were captured within the other smaller squares (data not shown).

EXAMPLE 4

Robust binding of fimbriated *E. coli* to polystyrene and quartz substrates, previously modified by covalent attachment of RNAse B One-well microtiter plates manufactured from polystyrene were carboxylated by Polyfiltronics, Inc. (Rockland, MA). The carboxyl groups of this substrate (designated as PS-COOH) were converted to N-hydroxysuccinithide (NHS) esters using 1-(3-dimethylaminopropyl)-3-ethylcarbodiimide hydrochloride (EDC) in 0.5M MES buffer, pH 6.0 as shown in FIG. 16A. Reaction with 250 µg/ml RNAse B in 0.1M borate buffer, pH 8.5, for 16 hours at room temperature afforded covalently linked RNAse B to the polystyrene substrate.

Fimbriated *E. coli* are firmly bound to this substrate. Bound cells were still attached after vigorous washing (from a distilled water faucet). In contrast, cells bound to RNAse adsorbed to silanized quartz (see previous examples) were easily dislodged by vigorous washing. Hence covalent attachment of RNAse B to substrates allows cells to be robustly captured; vigorous washing may help ensure that recombinant cells are captured only at anchor sites. Quartz substrates could be modified by covalent attachment of RNAse B in an analogous fashion. Quartz wafers were first silanized with aminopropyltriethoxysilane as described (D. Kleinfeld, K. H. Kahler, and P. E. Hockberger (1988) J. Neurosci 8: 409–4120). Following reaction of the primary amino groups with succinic anhydride in DMF for 16 hours at room temperature, the resulting carboxyl groups were converted to NHS esters using EDC. Reaction with RNAse B was performed as described above.

Fimbriated *E. coli* were also firmly bound to this silanized quartz substrate (data not shown).

Figure 7:
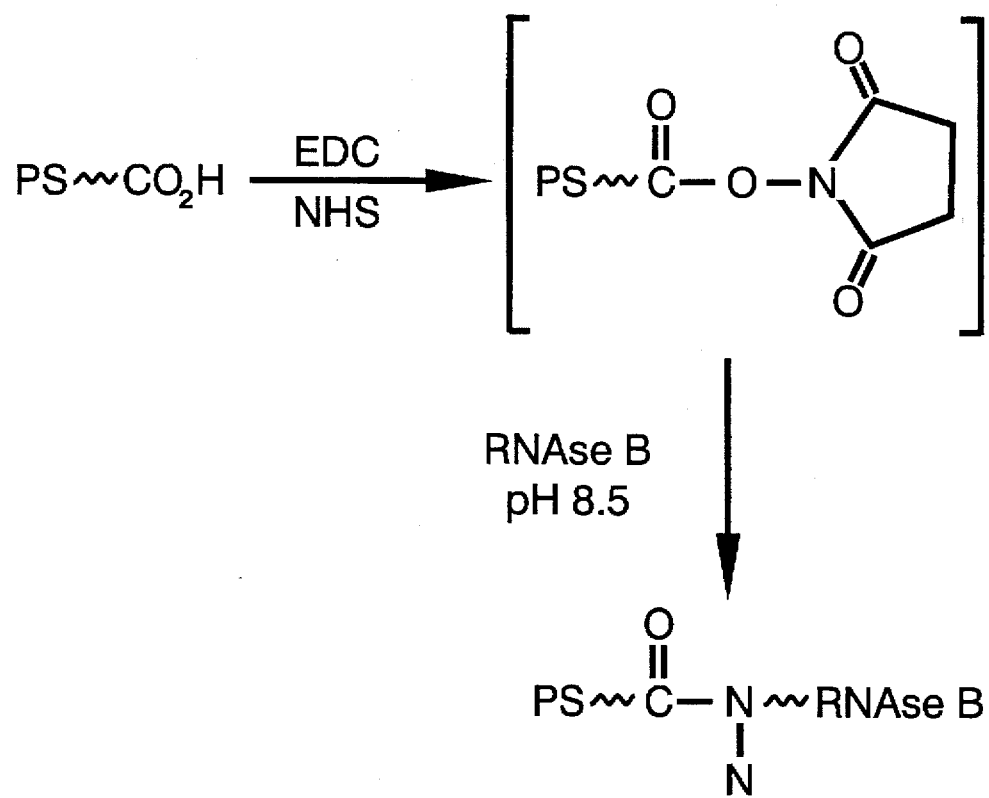
FIG. 7 shows an example of a chemical reaction that may be used to immobilize RNAse B to polystyrene (see example 4)

FIG. 7 is a reaction scheme showing covalent attachment of RNAse B to carboxylated polystyrene (PS-COOH).

EXAMPLE 5

Complementation of a fimH deletion strain of *E. coli* with plasmids bearing the fimH gene.

*E. coli* ORN133 (L. Maurer and P. E. Orndorff (1987) J. Bacteriol. 169: 640–645) containing a deletion in the fimH gene (which renders the cells unable to bind to mannose compounds) was transformed with plasmid pRT4 (R. Tewari, J. I. MacGregor, T. Ikeda, J. R. Little, S. J. Hultgren, and S. N. Abraham (1993) J. Biol. Chem. 268: 3009–3015) containing the fimH gene under the control of the strong lac promoter and plasmid pSH2 (R. A. Hull, R. E. Gill, P. Hsu, B. H. Minshew, and S. Falkow (1981) Infect. Immun. 33: 933–938), which contains the fimH gene behind its native promoter. Suspensions of strains ORN133 with and without pRT4 and pSH2 were incubated with RNAseB adsorbed to silanized quartz as described in Example 2. Wafers were viewed under light microscopy.

Strain ORN133 lacking the fimH gene failed to bind to the RNAse B wafers, whereas strains ORN133(pRT4) and ORN133(pSH2) bound confluently.

In a second experiment, strain ORN133 was transformed with plasmid pRT4, and the transformation mix (typically containing approximately 0.1% transformed cells) was exposed to RNAseB covalently linked to a polystyrene substrate (see EXAMPLE 4). Substrates were then viewed under light microscopy. Whereas untransformed ORN133 cells showed no binding to the substrate, transformed cells were bound confluently by the RNAseB coated surface in an analogous fashion to that shown in Figure x. This experiment shows that transformed cells can be captured from a transformation mix with an RNAse B substrate.

INCORPORATION BY REFERENCE

All publications and patent applications mentioned in this specification are indicative of the level of skill of those skilled in the art to which this invention pertains. All publications and patent applications referenced in the specification are herein incorporated by reference to the same extent as if each individual publication or patent application was specifically and individually indicated to be incorporated by reference.

EQUIVALENTS

Although only a few embodiments have been described in detail above, those having ordinary skill in the molecular biology art will clearly understand that many modifications are possible in the preferred embodiment without departing from the teachings thereof. All such modifications are intended to be encompassed within the following claims. The foregoing written specification is considered to be sufficient to enable skilled in the art to which this invention pertains to practice the invention. Indeed, various modifications of the above-described modes for carrying out the invention which are apparent to those skilled in the field of molecular biology or related fields are intended to be within the scope of the following claims,

What is claimed is:

1. A host organism capture system comprising:
    a solid support; and
    a plurality of binding moieties attached to the solid support, the binding moieties being members of binding pairs, the complementary member of the binding pairs being expressed on the surface of a host organism, wherein the binding moieties are located in a plurality of discrete anchor sites, each anchor site having dimensions, such that only a single host organism can bind to a single anchor site.

2. The host organism capture system of claim 1 wherein the binding moiety is RNAse B.

3. A method for fabricating a host organism capture system according to claim 1, said method comprising:
    treating a surface of a solid support to facilitate attachment of a binding moiety;
    coating the surface with a photoresist agent;
    subjecting the surface to ultraviolet radiation through a mask for creating regions of unmasked surface;
    contacting the surface with a solution of the binding moiety such that the binding moiety attaches only at regions of unmasked surface; and
    removing any remaining photoresist agent.

4. The method of claim 3, wherein the solid support is quartz.

5. The method of claim 3, wherein the step of treating the surface of the solid support to facilitate attachment of a binding moiety includes treatment with n organosilane reagent.

6. A method of analyzing individual cells of interest, said method comprising
    contacting a liquid containing a cell population to a host capture system of claim 1, whereby single cells are bound to the anchor regions.

7. A method according to claim 6, said method further comprising the step of lysing cells bound to the anchor sites, whereby polynucleotides are released.

8. A method according to claim 7, said method comprising the step of amplifying a subset of the released polynucleotides, wherein nucleic acid amplification products are produced.

9. A method according to claim 8, further comprising the step of sequencing the nucleic acid amplification products.

10. A host organism capture system according to claim 1, said system further comprising,
    a plurality of incubation chambers, each of the chambers comprising an input port, an output port, and chamber walls, wherein the chamber walls form the input and output ports, and wherein the output ports enclose the anchor sites in a liquid occlusive manner and the incubation chambers are in register with the anchor sites.

11. A host capture system according to claim 10, said system further comprising a sealing gasket, wherein the gasket forms a liquid occlusive seal between the output port and the solid support.

12. A host organism capture system according to claim 10, wherein the chamber walls of the incubation chambers are formed from the solid support.

13. A host capture system according to claim 10, comprising a non-specific polynucleotide capture region on the walls of the incubation chambers.

14. A host capture system according to claim 10, comprising a sequence specific polynucleotide capture region on the walls of the incubation chambers.

15. A host capture system according to claim 10, wherein the binding moiety is RNase B.

16. A host capture system according to claim 10, comprising a plurality of non-specific polynucleotide capture regions, therein the non-specific polynucleotide capture regions are located adjacent to the anchor sites.

17. A host organism capture system according to claim 10, said system further comprising a plurality of cell capture regions, wherein each of the cell capture regions is formed of immobilized second binding moieties that are immobilized at sites in register with the anchor sites.

18. A host organism capture system according to claim 17, wherein the cell capture regions are of a size sufficient to bind a plurality of cells.

19. A host organism capture system according to claim 17, wherein the first biding moieties of the anchor sites are the same as the second binding moieties of the cell capture regions.

20. A host organism capture system according to claim 17, said system further comprising a cover plate having a top and bottom surface, wherein the cell capture regions are on the bottom surface of the cover plate and the cell capture regions are in register with the input ports.

21. A host organism capture system of claim 20, wherein the cell capture regions are on the incubation chamber walls.

22. A host organism capture system according to claim 20, said system further comprising a plurality of second cell capture regions, wherein said second cell capture regions are present on the chamber walls.

23. A method of analyzing individual cells of interest, said method comprising
    exposing a liquid containing a cell population to the host capture system of claim 10, wherein single cells are bound to the anchor sites,
    propagating the bound single cells within the incubation chamber, wherein progeny
    cells not bound to the anchor site are produced.

24. A method according to clam 23, wherein the host organism capture system further comprises a sealing gasket wherein the gasket forms a liquid occlusive seal between the output port and the solid support.

25. A method according to claim 23, wherein walls of the incubation chambers are formed from the solid support.

26. A method according to claim 23, wherein the host organism capture system further comprises a cover plate having a top and bottom surface, having cell capture regions on the bottom surface of the cover plate and the cell capture regions are in register with the input ports.

27. A method according to claim 23, wherein the host organism capture system further comprises a non-specific polynucleotide capture region on the walls of the incubation chambers.

28. A method according to claim 23, wherein the host organism capture system further comprises a sequence-specific polynucleotide capture region on the walls of the incubation chambers.

29. A method according to claim 23, wherein the binding moiety is RNase B.

30. A method according to claim 23, wherein the host organism capture system further comprises a plurality of non-specific polynucleotide capture regions, wherein the non-specific polynucleotide capture regions are located adjacent to the anchor sites.

31. A method according to claim 23, said method further comprising the steps of contacting the progeny cells with a cell capture region wherein the cell capture region is formed of immobilized second binding moieties that are immobilized at a location in register with the anchor sites.

32. A method according to claim 31 wherein cell capture regions are on the incubation chamber walls.

33. A method according to claim 31, wherein the host organism capture system further comprises a plurality of second cell capture regions, wherein said second cell capture regions are present on the chamber walls.

34. A method according to claim 31, wherein the cell capture regions are of a size sufficient to bind a plurality of cells.

35. A method according to claim 31, wherein the first binding moieties of the anchor site are the same as the second binding moieties of the cell capture regions.

36. A method according to claim 23, said method further comprising the step of lysing the progeny cells, whereby polynucleotides are released.

37. A method according to claim 36, wherein a subset of the released polynucleotides are amplified in a nucleic acid amplification reaction.

38. A method according to claim 36, wherein the released polynucleotides are sequenced.

* * * * *